(12) United States Patent
Chen et al.

(10) Patent No.: US 10,386,361 B2
(45) Date of Patent: Aug. 20, 2019

(54) LONG TERM HEMATOPOIETIC STEM CELL SPECIFIC REPORTER MOUSE AND USES THEREOF

(71) Applicant: The Board of Trustees of the Leland Stanford Junior University, Stanford, CA (US)

(72) Inventors: James Y. Chen, Gold River, CA (US); Masanori Miyanishi, Stanford, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 3 days.

(21) Appl. No.: 15/616,632

(22) Filed: Jun. 7, 2017

(65) Prior Publication Data

US 2017/0350879 A1    Dec. 7, 2017

Related U.S. Application Data

(60) Provisional application No. 62/346,857, filed on Jun. 7, 2016.

(51) Int. Cl.

| | |
|---|---|
| G01N 33/50 | (2006.01) |
| C12N 5/0789 | (2010.01) |
| A61K 49/00 | (2006.01) |
| A01K 67/027 | (2006.01) |
| C07K 14/47 | (2006.01) |
| C07K 14/435 | (2006.01) |
| C12N 15/10 | (2006.01) |

(52) U.S. Cl.
CPC ..... *G01N 33/5073* (2013.01); *A01K 67/0275* (2013.01); *A61K 49/0008* (2013.01); *C07K 14/43595* (2013.01); *C07K 14/47* (2013.01); *C07K 14/4702* (2013.01); *C12N 5/0647* (2013.01); *A01K 2227/105* (2013.01); *A01K 2267/03* (2013.01); *C12N 15/102* (2013.01); *C12N 2510/00* (2013.01); *G01N 2333/47* (2013.01)

(58) Field of Classification Search
CPC ........... G01N 33/5073; G01N 2333/47; A01K 67/0275; A01K 2227/105; A01K 2267/03; A61K 49/0008; C07K 14/43595; C07K 14/47; C07K 14/4702; C12N 5/0647; C12N 15/102; C12N 2510/00
See application file for complete search history.

(56) References Cited

U.S. PATENT DOCUMENTS

| | | |
|---|---|---|
| 7,166,444 B2 | 1/2007 | Lukyanov et al. |
| 7,338,782 B2 | 3/2008 | Lukyanov et al. |
| 7,338,783 B2 | 3/2008 | Lukyanov et al. |
| 7,338,784 B2 | 3/2008 | Lukyanov et al. |
| 7,338,785 B2 | 3/2008 | Lukyanov et al. |
| 7,344,862 B2 | 3/2008 | Lukyanov et al. |
| 7,442,521 B2 | 10/2008 | Lukyanov et al. |
| 7,442,522 B2 | 10/2008 | Lukyanov et al. |
| 7,537,915 B2 | 5/2009 | Lukyanov et al. |
| 8,012,682 B2 | 9/2011 | Lukyanov et al. |
| 2011/0027235 A1* | 2/2011 | Gregory .................. C12N 9/22 424/93.7 |
| 2015/0223436 A1* | 8/2015 | Rossi .................. C12Q 1/6897 800/18 |

OTHER PUBLICATIONS

Clark et al. "A future for transgenic livestock." Nat Rev Genet. Oct. 2003;4(10):825-33. (Year: 2003).*
Ristevski S. "Making better transgenic models: conditional, temporal, and spatial approaches."Mol Biotechnol. Feb. 2005;29(2):153-63. (Year: 2005).*
Sigmund CD "Viewpoint: are studies in genetically altered mice out of control?" S Arterioscler Thromb Vasc Biol. Jun. 2000;20(6): 1425-9. (Year: 2000).*
Carmo et al. "Modeling Alzheimer's disease in transgenic rats." Mol Neurodegener. Oct. 25, 2013;8:37. (Year: 2013).*
Fosberg et al. "Differential expression of novel potential regulators in hematopoietic stem cells." PLoS Genet. Sep. 2005;1(3):e28. (Year: 2005).*
Chen et al. "Hoxb5 marks long-term haematopoietic stem cells revealing a homogenous perivascular niche." Nature. Feb. 11, 2016; 530(7589): 223-227 (Year: 2016).*
Upadhaya et al. "New genetic tools for the in vivo study of hematopoietic stem cell function.."E xp Hematol. May 2018;61:26-35 (Year: 2018).*
Szade et al."Where Hematopoietic Stem Cells Live: The Bone Marrow Niche." Antioxid Redox Signal. Jul. 10, 2018;29(2):191-204 (Year: 2018).*
Tjin et al. "Imaging methods used to study mouse and human HSC niches: Current and emerging technologies." Bone. Feb. 2019; 119:19-35 (Year: 2019).*
Ebina. W. "Combinatorial Pathway Modulation Toward Ex Vivo Maintenance and Propagation of Hematopoietic Stem Cells." Doctoral dissertation, Harvard University, Graduate School of Arts & Sciences. (Year: 2016).*

(Continued)

*Primary Examiner* — Titilayo Moloye
(74) *Attorney, Agent, or Firm* — Pamela J. Sherwood; Bozicevic, Field & Francis LLP

(57) ABSTRACT

Hoxb5 identifies long-term hematopoietic stem cells. Expression of Hoxb5 distinguishes between LT-HSCs and non-LT-HSCs, and the marker identifies substantially all LT-HSC in the bone marrow. By utilizing fluorescent proteins under the endogenous expression control of Hoxb5, LT-HSC can be monitored and isolated, including without limitation detection and monitoring of HSC in bone morrow; production of LT-HSC from pluripotent stem cells such as iPS cells; for analysis of early stage LT-HSC; in screening methods for expansion and manipulation of LT-HSC, and the like.

7 Claims, 26 Drawing Sheets
(23 of 26 Drawing Sheet(s) Filed in Color)
Specification includes a Sequence Listing.

(56) References Cited

OTHER PUBLICATIONS

Morikawa et al. "Use of Imaging Techniques to Illuminate Dynamics of Hematopoietic Stem Cells and Their Niches." Front Cell Dev Biol. 2017 (Year: 2017).*
Lu et al., "Tracking single hematopoietic stem cells in vivo using high-throughput sequencing in conjunction with viral genetic barcoding", Nature Biotechnol., Oct. 2011, pp. 928-933, 29(10), Macmillan Publishers Limited, London, United Kingdom.
Acar et al., "Deep imaging of bone marrow shows non-dividing stem cells are mainly perisinusoidal", Nature, Oct. 1, 2015, pp. 126-130, 526, (7571), Nature Publishing Group, London, United Kingdom.
Gazit et al., "Fgd5 identifies hematopoietic stem cells in the murine bone marrow", J. Exp. Med. Jun. 23, 2014, pp. 1315-1331, 211, The Rockefeller University Press, New York, NY.
Hills et al., "Hoxb4-YFP reporter mouse model: a novel tool for tracking HSC development and studying the role of Hoxb4 in hematopoiesis", Blood, Mar. 31, 2011, pp. 3521-3528, vol. 117, No. 13, The American Society Hematology, Washington, D.C.
Yamamoto et al., "Clonal analysis unveils self-renewing lineage-restricted progenitors generated directly from hematopoietic stem cells", Cell, Aug. 29, 2013, pp. 1112-1126, 154, Elsevier, Amsterdam, Netherlands.
Fairman et al, "Upregulation of CD11A on hematopoietic stem cells denotes the loss of long-term reconstitution potential", Stem Cell Reports, Nov. 11, 2014, pp. 707-715, vol. 3, Issue 5, Elsevier, Amsterdam, Netherlands.
Oguro et al., "SLAM family markers resolve functionally distinct subpopulations of hematopoietic stem cells and multipotent progenitors", Cell Stem Cell, Jul. 3, 2013, pp. 102-116, 13, Elsevier, Amsterdam, Netherlands.
Forsberg et al., "Molecular signatures of quiescent, mobilized and leukemia-initiating hematopoietic stem cells", PLoS ONE, Jan. 2010, p. 1-11, PLoS ONE, San Francisco, CA.

* cited by examiner

FIG. 1B

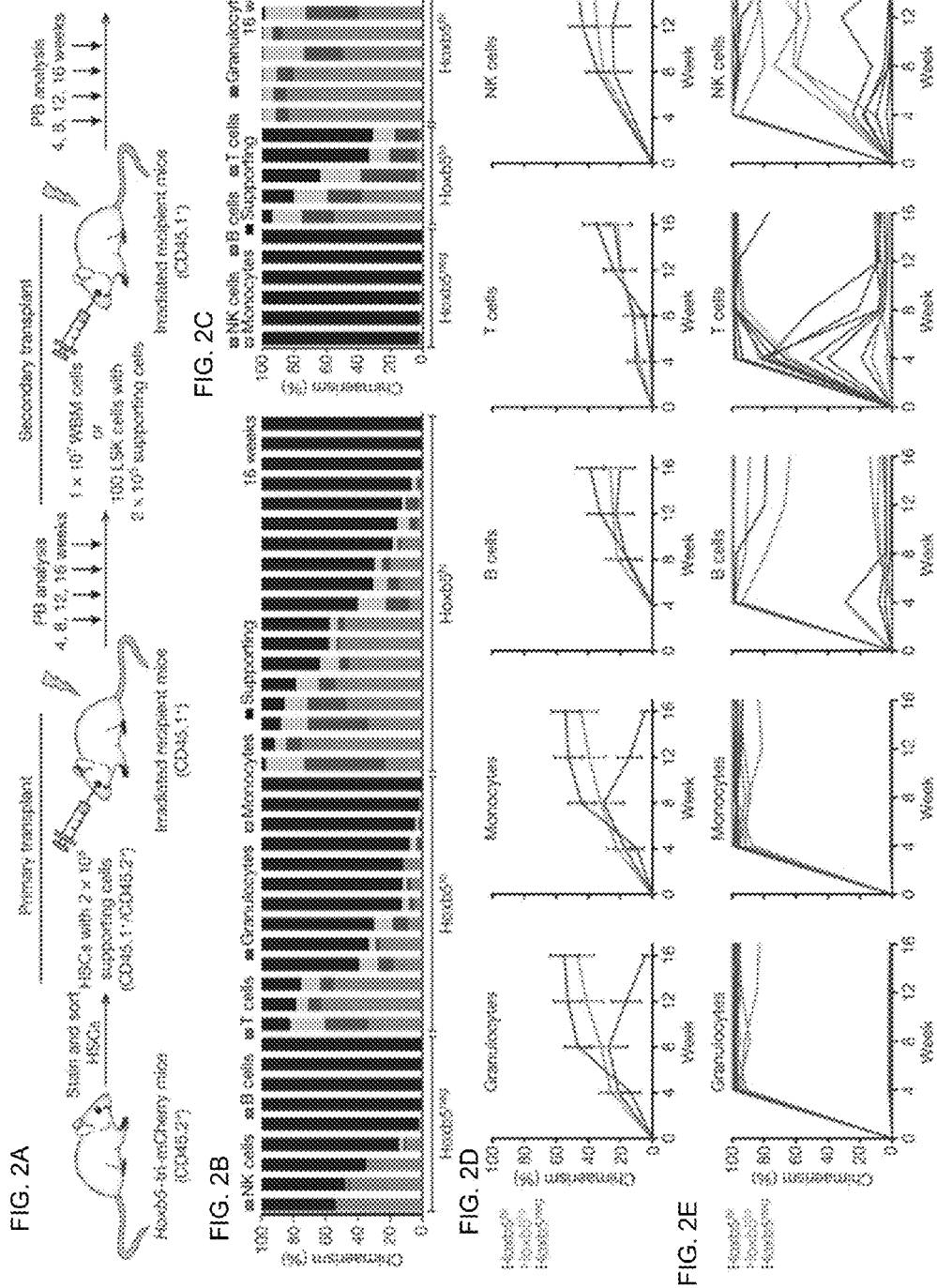

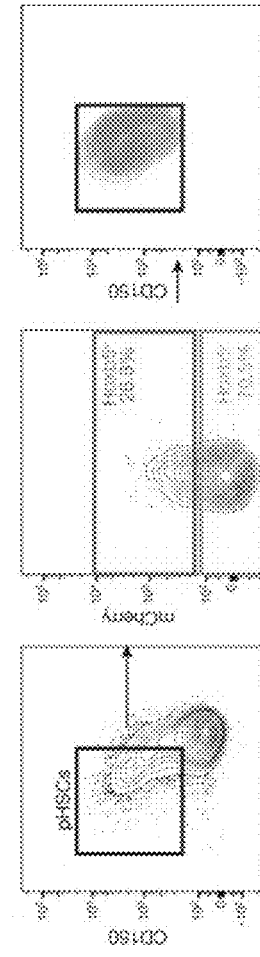
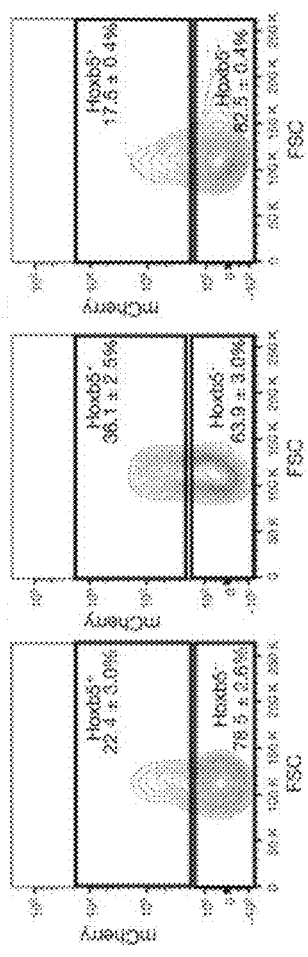
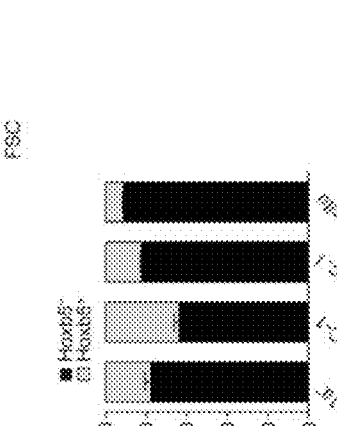
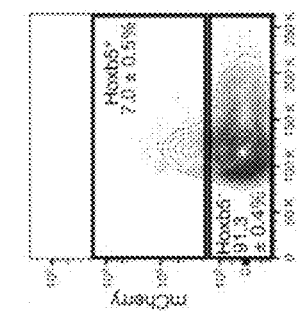

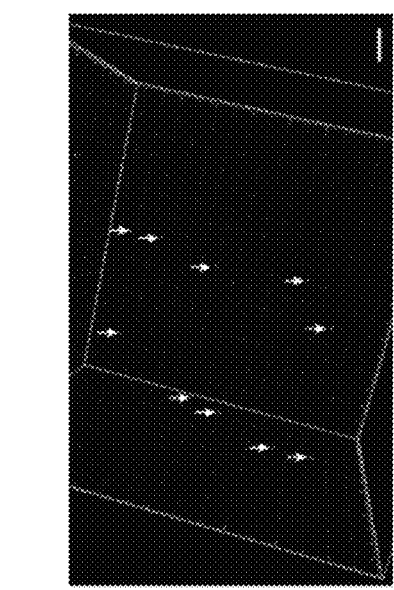
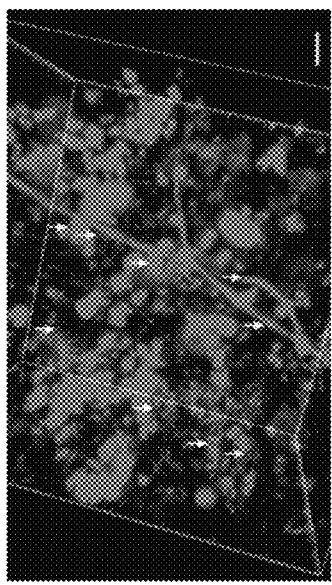
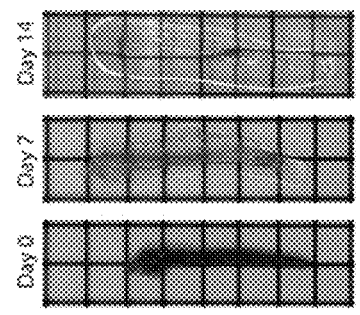
FIG. 4A
FIG. 4B
FIG. 4C
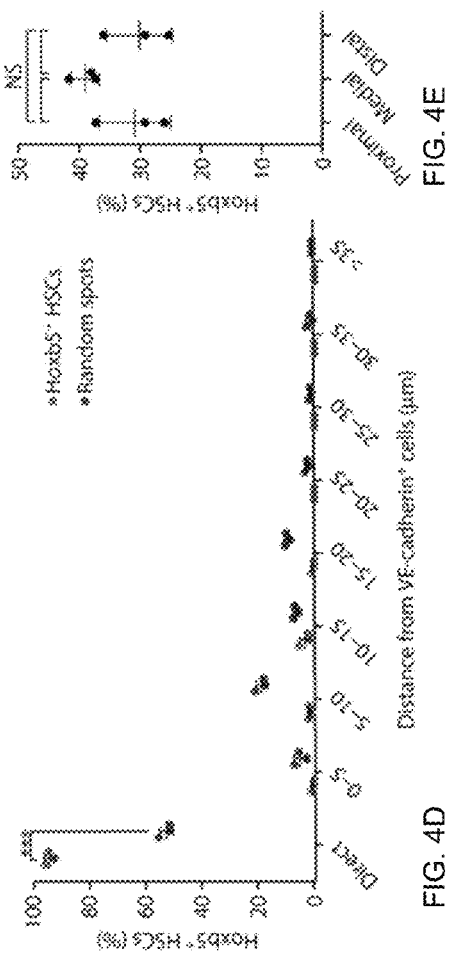
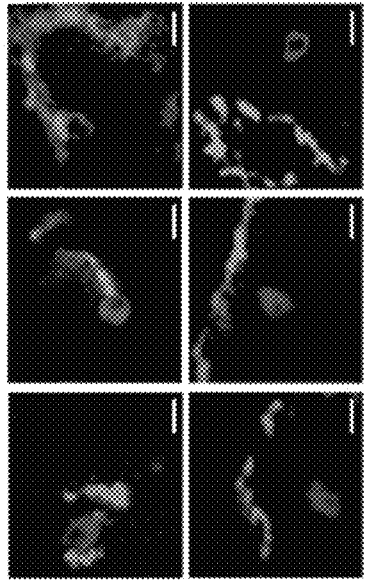
FIG. 4D
FIG. 4E

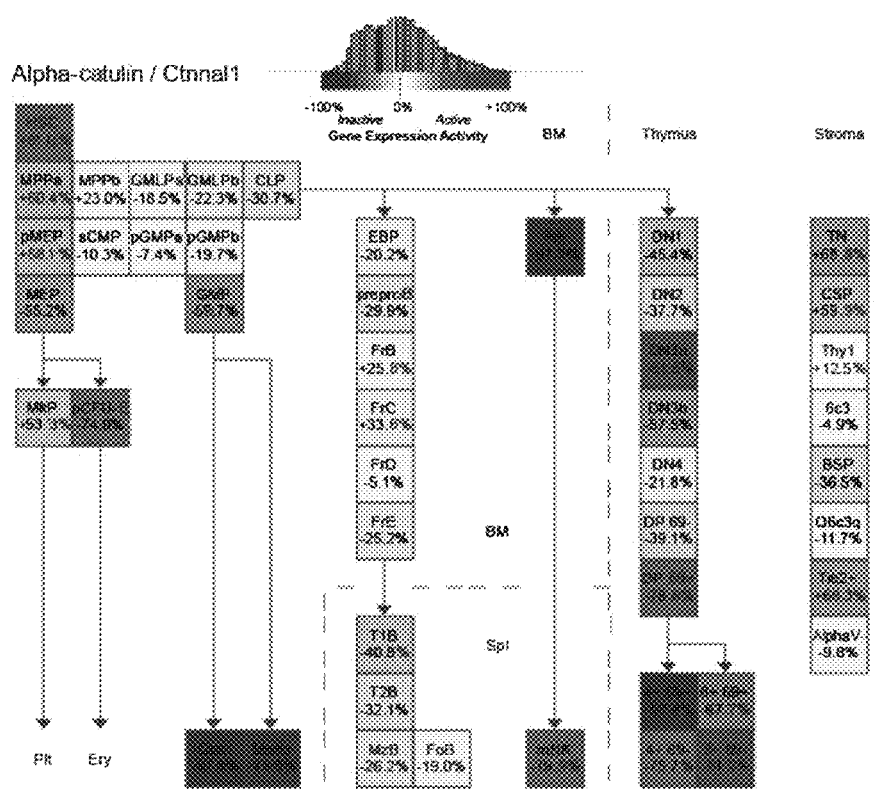
FIG. 5B(ii)

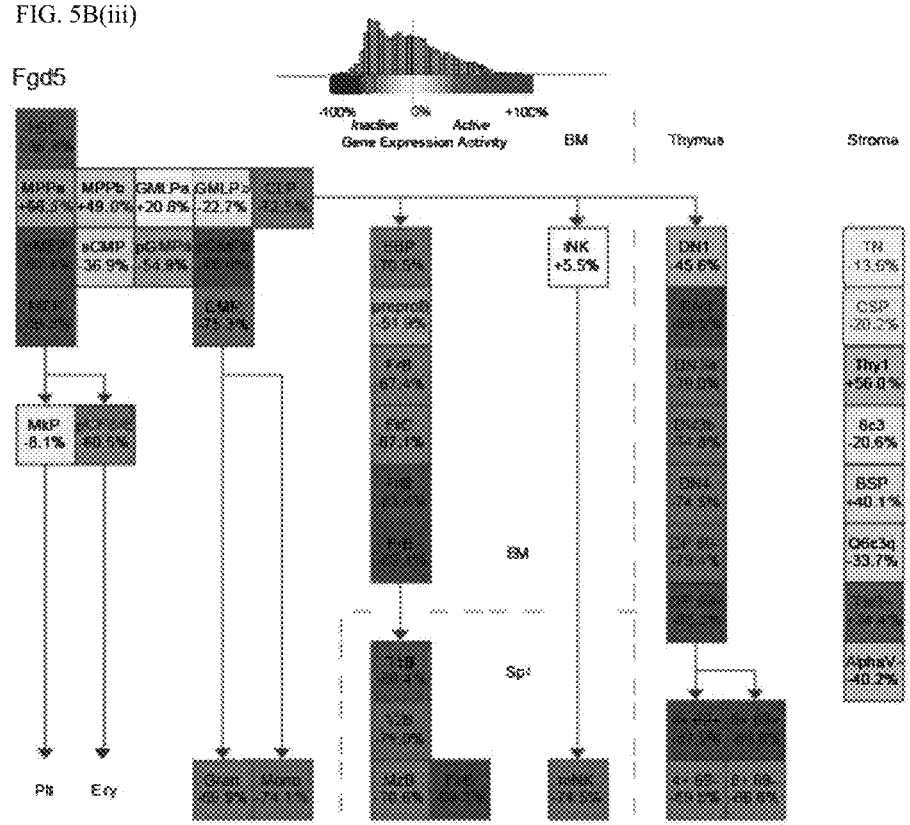
FIG. 5B(iii)

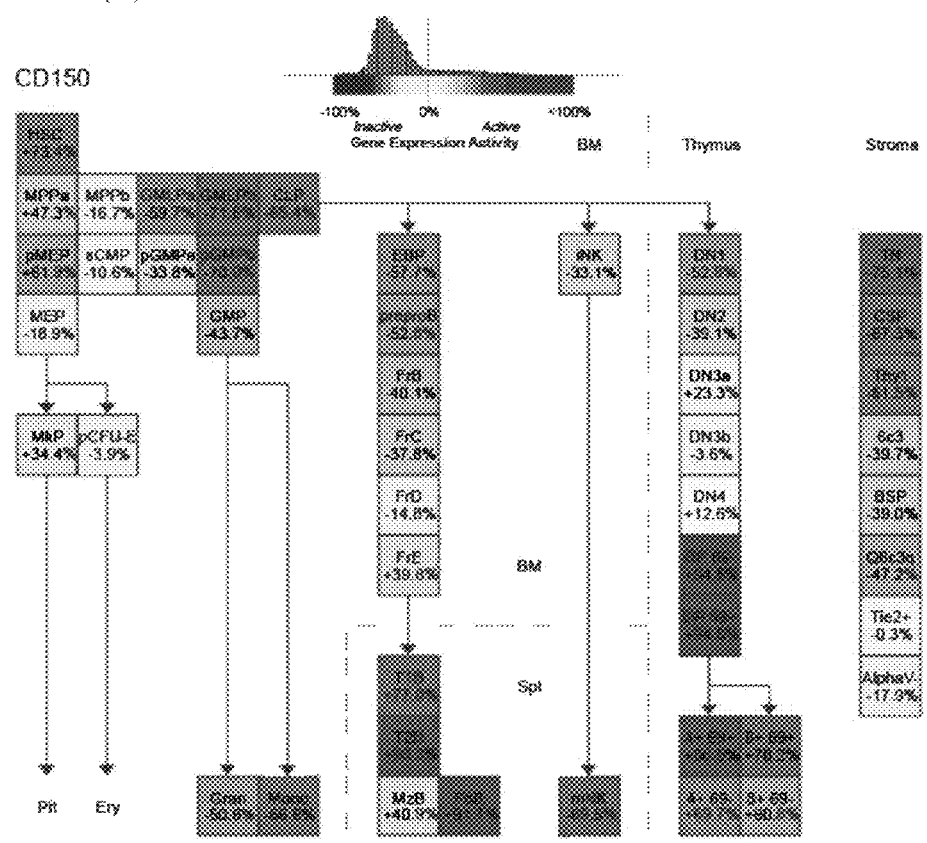
FIG. 5B(iv)

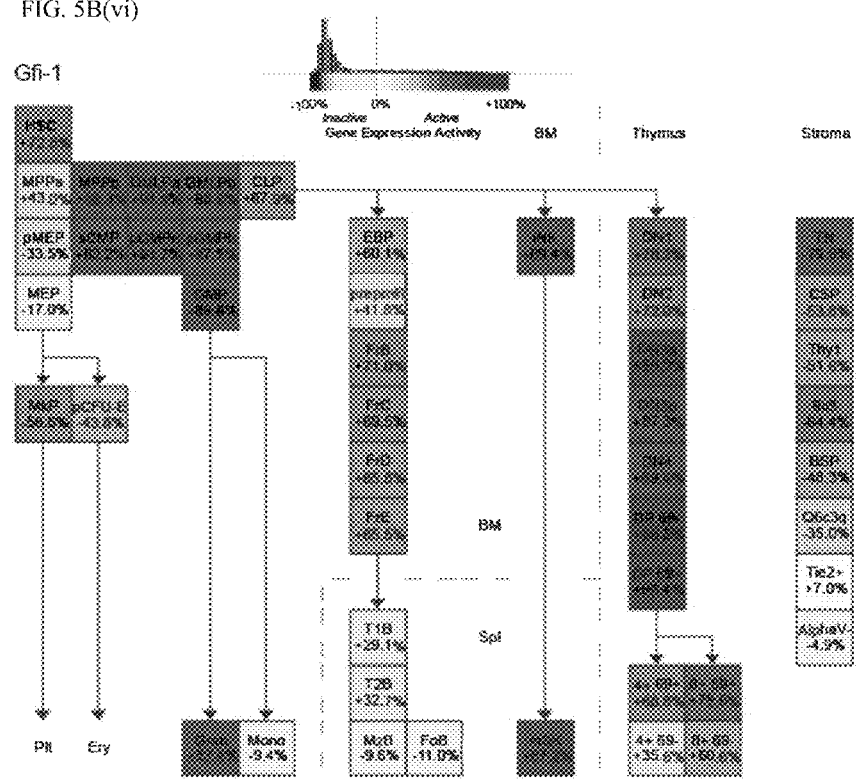
FIG. 5B(vi)

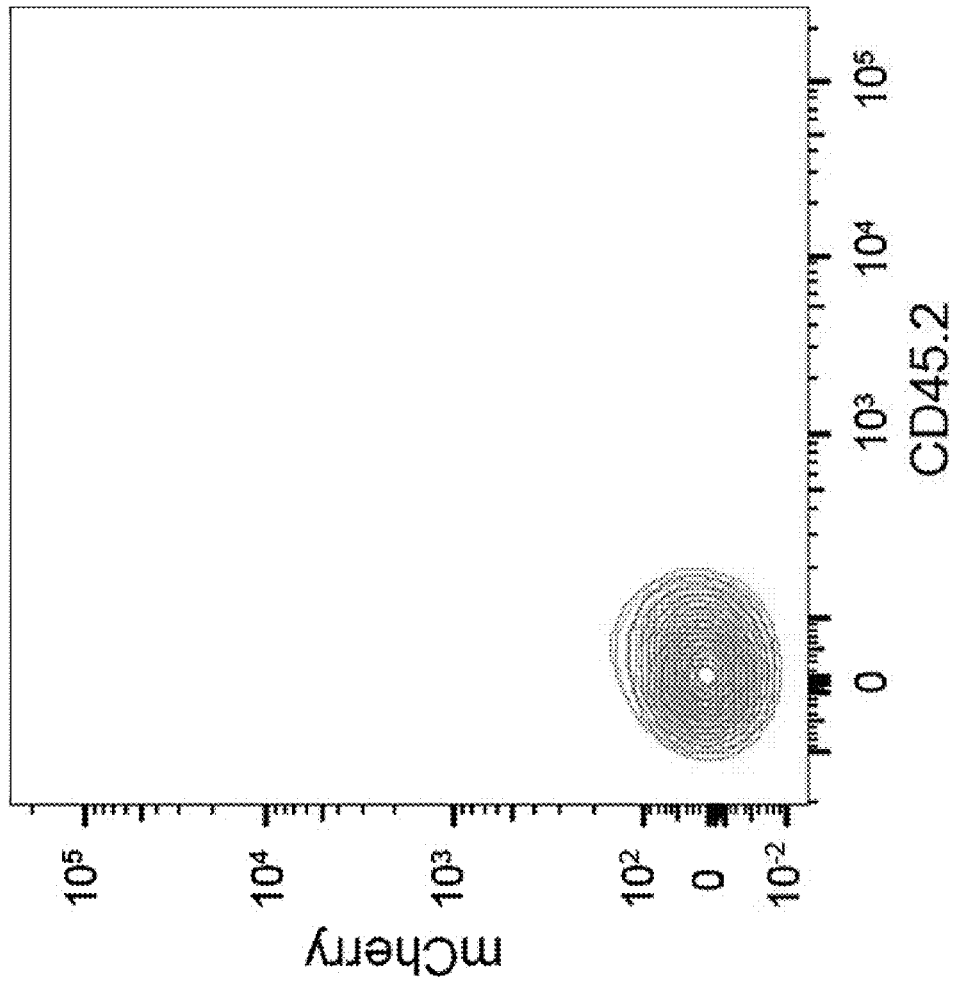

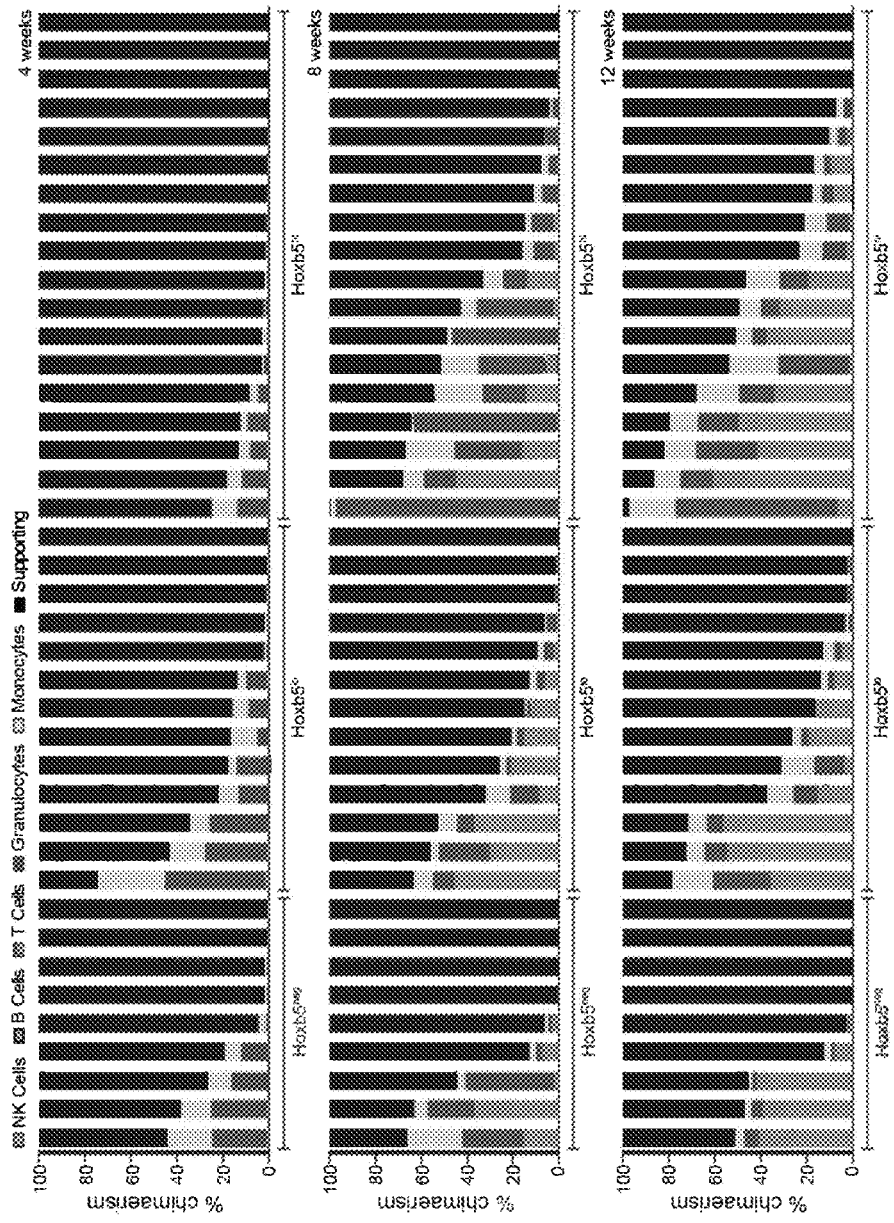

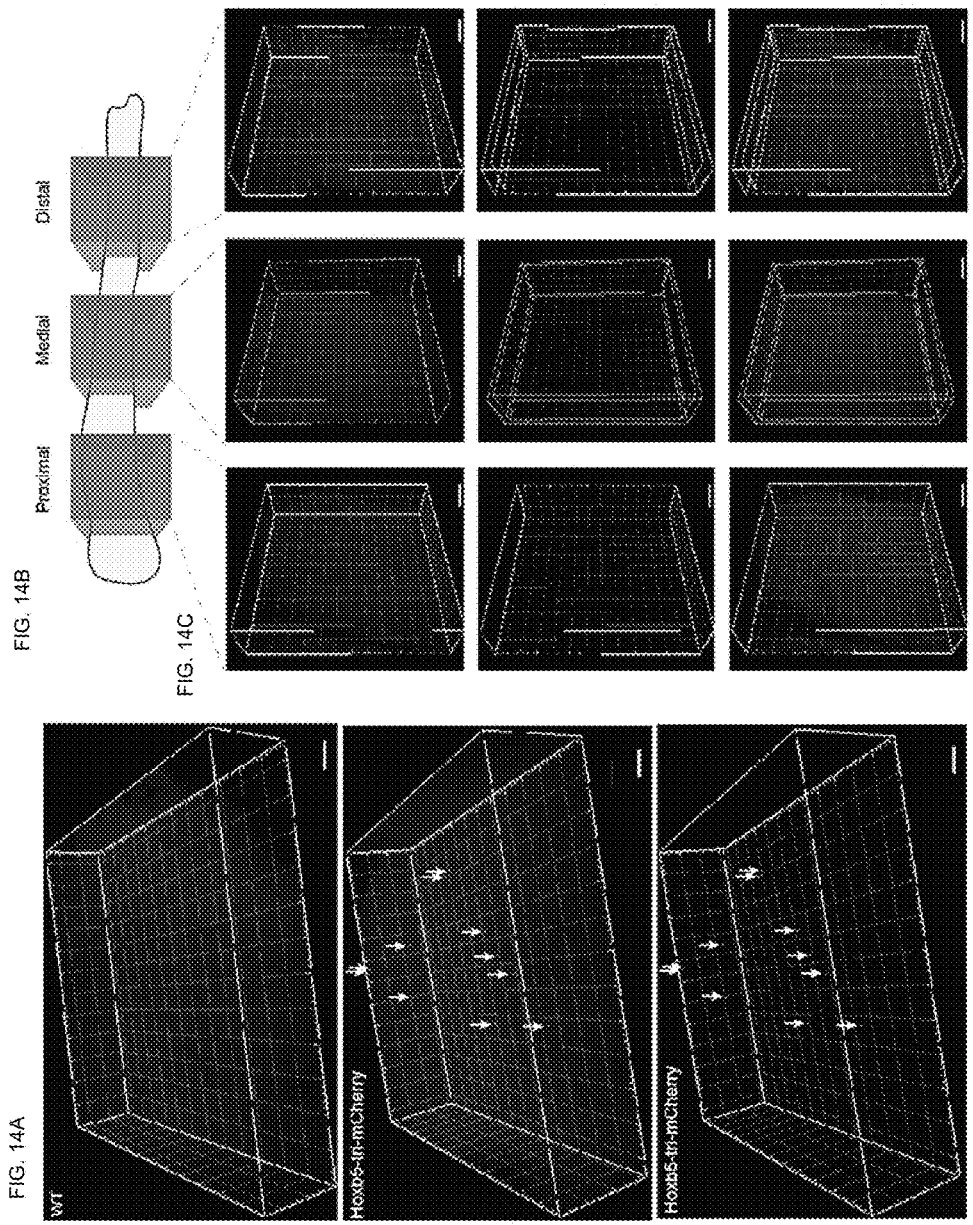

LONG TERM HEMATOPOIETIC STEM CELL SPECIFIC REPORTER MOUSE AND USES THEREOF

CROSS REFERENCE

This application claims benefit of U.S. Provisional Patent Application No. 62/346,857, filed Jun. 7, 2016, which applications are incorporated herein by reference in their entirety.

FEDERALLY SPONSORED RESEARCH AND DEVELOPMENT

This invention was made with Government support under contract CA086065, HL099999, and HL058770 awarded by the National Institutes of Health. The Government has certain rights in the invention.

BACKGROUND

The two defining criteria of stem cells are multi-potency and self-renewal. Hematopoietic Stem Cells (HSCs) are the only cells within the hematopoietic system that possess the potential for both multi-potency and self-renewal. In the case of HSC, multi-potency is the ability to differentiate into all functional blood cells, while self-renewal is the ability to give rise to identical daughter HSCs without differentiation.

The initial prospective purification of hematopoietic stem cells from mouse BM was achieved utilizing multi-color fluorescence-activated cell sorting and monoclonal antibodies. The resultant population of enriched mouse HSCs had a surface marker phenotype of Thy-1$^{low}$ Lin (Lineage-markers)$^-$Sca-1$^+$, and represented approximately 0.05% of the mouse adult BM cells. Since these initial studies, mouse HSCs have been more extensively purified by identifying and then utilizing additional cell-surface markers to distinguish them from other cells in BM; these included, but were not exclusively single cells that could self-renew and give long-term multilineage maturation. The initial population has been shown to include at least 3 multipotent populations: Long-Term (LT)-HSC, Short-Term (ST)-HSC, and Multi-Potent Progenitor (MPP, a cell population that has lost the self-renewal capacity of HSC). Despite the fact that hematopoietic tissues contain both stem and progenitor cells, rapid and sustained engraftment of syngenic and even of H2 incompatible allogenic hosts can only be achieved with HSC.

The mammalian blood system contains more than ten distinct mature cell types including red blood cells (erythrocyte), megakaryocytes/platelets, myeloid cells (monocyte/macrophage and granulocytes), mast cells, T- and B-lymphocytes, natural killer (NK) cells and dendritic cells (DCs). Such diverse cell types are all derived from a common progenitor cell, i.e. from HSCs. Analyses have shown a hierarchical structure in hematopoietic development in which multi-potency is progressively restricted. HSCs initially give rise to the MPPs which no longer possess self-renewal ability yet keeping full-lineage differentiation potential. Further downstream, MPPs advance to oligopotent progenitors, the common lymphoid progenitor (CLP) and the common myeloid progenitor (CMP). Collectively these oligopotent progenitors then give rise to all the lineage-committed effector cells of the hematopoietic system.

Human HSCs were isolated using similar technologies to those used for mouse HSCs, i.e. isolation of cells representing different stages of differentiation on the basis of cell-surface marker phenotype, coupled with functional assays. For human hematopoiesis, the property of long-term reconstitution of the various cell subsets can be evaluated in xenotransplantations models, utilizing immuno-deficient mice, sometimes transplanted with fetal human hematolymphoid organs for irradiation-resonstitution assays.

In contrast to the high turnover of lineage-restricted progenitors, most of HSCs reside in the 'quiescent' $G_0$ phase of the cell cycle. TGF-β/Smad signaling is one of the responsible pathways that maintain quiescence of HSCs, although due to the high redundancy of the Smad molecules (which are the intracellular transducer of TGF signaling), and early embryonic lethality of most Smad and TGF-β knockout mouse models, in vivo elucidation of the role of the TGF/Smad signaling pathway in HSC function has proven difficult. Another proposed cue for HSC quiescence is Ang-1/Tie2. Tie2 is a receptor tyrosine kinase expressed on endothelial cells and HSCs.

The blood system reflects the balance of two essential abilities of HSC, self-renewal and differentiation. Intensive studies have revealed the hierarchical structure of the blood system and key molecules regulating LT-HSC. However, the entire picture of the molecular interactions orchestrating LT-HSC fate is yet unclear. Synergies between highly developed biological and molecular approaches and rapidly emerging systems approaches are needed to integrate and accelerate understanding of this cell population.

SUMMARY

It is demonstrated herein that expression of Hoxb5 identifies long-term hematopoietic stem cells. Expression of Hoxb5 distinguishes between LT-HSCs and non-LT-HSCs, and the marker identifies substantially all LT-HSC in the bone marrow. By utilizing fluorescent proteins under the endogenous expression control of Hoxb5, LT-HSC can be monitored and isolated, including without limitation detection and monitoring of HSC in bone morrow; production of LT-HSC from pluripotent stem cells such as iPS cells; for analysis of early stage LT-HSC; in screening methods for expansion and manipulation of LT-HSC, and the like.

In some embodiments a transgenic mouse model for analysis of LT-HSC is provided, in which one or more marker sequences are operably linked to the regulatory sequences that control Hoxb5 expression. Also provided are cells derived from a transgenic mouse, which cells include without limitation, embryonic stem cells, induced pluripotent stem cells, umbilical cord stem cells, bone marrow cells including short term and long term hematopoietic stem cells, peripheral blood derived stem cells; etc. Cells of interest may include purified populations of LT-HSC purified or differentiated from any of these cell populations. In some such embodiments the marker sequence is integrated at the chromosomal location of a native Hoxb5 gene. In other embodiments the regulatory elements that control Hoxb5 expression are isolated and operably joined to a marker sequence. To provide for LT-HSC specific expression, sequences encoding the marker are preferably transcribed by the endogenous Hoxb5 promoter regulation. The sequence encoding the marker may be, for example, expressed in tandem with Hoxb5 when separated by an internal ribosome entry site, (IRES); when separated by a peptide cleavage site, e.g. P2A self-cleaving peptide, and the like.

The marker sequence may be a protein detectable by luminescent or fluorescent properties, including without limitation luciferase and variants thereof; *Aequorea victoria* sourced fluorescent proteins and derivatives there, including without limitation Blue-Fluorescent Protein (BFP), Cyan-Fluorescent Protein (CFP), green fluorescent protein (GFP), enhanced GFP with red-shifted excitation (EGFP), enhanced Yellow-Fluorescent Protein (EYFP), photoactivatable green fluorescent protein (PA-GFP), etc., *Discoma* species fluorescent protein, e.g. dsRed, mFruits, mCherry, etc.; TagR-FPs; *Entacmaea quadricolor* fluorescent protein, e.g. eqFP611; Dronpa; EosFP; and the like as known in the art. Such fluorescent and bioluminescent protein are known in the art, for example see any of U.S. Pat. Nos. 7,166,444; 7,338,784; 7,442,521; 7,537,915; 7,442,522; 7,338,782; 7,338,783; 7,338,785; 7,344,862; and 8,012,682. In some embodiments, tandem marker sequences are provided, e.g. two, three or more tandem coding sequences.

As an alternative to a directly detectable marker such as a fluorescent or luminescent protein, a marker may be any protein that does not interfere with the biology of the cell and that provides a unique sequence can be used as a marker, e.g. a cell surface protein to which antibody reagents are available, and the like.

Also provided are methods of using a transgenic mouse model for analysis of LT-HSC in which a marker sequence is operably linked to the regulatory sequences that control Hoxb5 expression. A method of isolating LT-HSC is provided, comprising selecting or removing cells from the transgenic mouse by selecting for cells expressing the marker sequence, e.g. by flow cytometry, etc. Isolated populations of LT-HSC are also provided, where the cells may be isolated from bone marrow, peripheral blood, etc. The cell populations may be substantially pure LT-HSC cells, e.g. at least about 50% of the population is LT-HSC, at least about 60% of the population is LT-HSC, at least about 70% of the population is LT-HSC, at least about 80% of the population is LT-HSC, at least about 90% of the population is LT-HSC, at least about 95% of the population is LT-HSC. Such isolated cells may be cultured in vitro, transplanted into an individual, used as a source of nucleic acids, proteins, etc.

Methods are provided for analysis of the growth and differentiation of LT-HSC, including screening of candidate agents that can either maintain, generate, and/or expand HSCs (LT-HSC or non LT-HSC) for a variety of implications, including bone marrow transplantation, gene therapy, drug toxicity screening, growth and/or differentiation, etc. by contacting the transgenic mouse or a population of cells, e.g. embryonic stem cells, induced pluripotent stem cells, umbilical cord stem cells, bone marrow cells including short term and long term hematopoietic stem cells, peripheral blood derived stem cells; etc. isolated or derived from the mouse, and determining the effect of a candidate agent or treatment on the expansion or differentiation of LT-HSC, which are conveniently monitored by quantitative or qualitative monitoring of the protein marker. For example the absolute number of LT-HSC can be determined, the number of LT-HSC relative to short term HSC, progenitor cells, and the like, and a candidate agent that increases numbers of LT-HSC in vitro or in vivo may be selected as an agent for LT-HSC expansion. Phenotypic attributes of LT-HSC may include, without limitation, self-renewal, multipotency, migration, attachment, proliferation, quiescence, etc.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1F: Multi-step unbiased screening identifies Hoxb5 as a candidate LT-HSC marker. FIG. 1A Microarray heat map depicting relative expression (pink, high; blue, low) of HSC-specific genes in haematopoietic and stromal populations. Each row represents a gene; each subcolumn a replicate microarray; each labelled column a category of cell populations. The 45 genes in the top panel displayed limited activity in all non-HSC populations examined. FIG. 1B Transcriptional profiling by RNA-seq of the 45 genes from a. Three genes (top panel) exceeded the estimated threshold for detection (FPKM>7.0) in HSCs while showing minimal expression (FPKM<2.5) in MPPa and MPPb populations. FIG. C Heterogeneity of expression for the three remaining candidate genes in HSCs as assessed by single-cell qPCR. FIG. 1D Venn diagram reflecting the four-step screen that identified Hoxb5 as an ideal candidate in the HSC transcriptome. FIG. 1E Targeting strategy to generate a triple-mCherry Hoxb5 knock-in mouse reporter line (Hoxb5-tri-mCherry). UTR, untranslated region; PGK, phosphoglycerate kinase I. FIG. 1F Hoxb5 reporter expression (red) in pHSCs and MPPs compared to wild-type controls (blue). Values indicate the percentage of mCherry$^+$ cells±s.d. in each fraction for n=3 mice.

FIG. 2A-2E: FIG. 2A Experimental schematic for long-term hematopoietic reconstitution assays. CD45.1$^+$ recipient mice were lethally irradiated and competitively transplanted with ten or three Hoxb5-tri-mCherry HSCs and 2×10$^5$ CD45.1$^+$/CD45.2$^+$ supporting cells. For secondary transplants, 1×10$^7$ whole bone marrow (WBM) cells or 100 sorted LSK cells were transferred from primary recipient mice. PB, peripheral blood. FIG. 2B Percentage chimaerism at 16 weeks in primary recipients receiving ten Hoxb5$^{neg}$ (n=9 mice), Hoxb5$^{lo}$ (n=13 mice), or Hoxb5$^{hi}$ (n=18 mice) pHSCs. Each column represents an individual mouse. FIG. 2C Percentage chimaerism at 16 weeks following whole bone marrow secondary transplant. FIG. 2D Average donor lineage contribution in ten-cell primary transplants. Error bars denote s.d. FIG. 2E Individual donor chimaerism by lineage in whole bone marrow secondary recipients. Each line represents an individual mouse (n=6 mice for Hoxb5$^{neg}$; n=5 mice for Hoxb5$^{lo}$; and n=8 mice for Hoxb5$^{hi}$).

FIG. 3A-3F: Previously defined HSC immunophenotypes contain Hoxb5$^-$ cells. Flow cytometry plots of bone marrow from 12-week-old mice depicting Hoxb5-tri-mCherry reporter activity in previously reported HSC immunophenotypes. FIG. 3A pHSC (LSK CD150$^+$CD34$^{-/lo}$Flk2$^-$) Hoxb5$^+$ (red) and Hoxb5$^-$ (blue). FIG. 3B CD11a$^-$ (LSK CD150$^+$CD34$^{-/lo}$CD11a$^-$). FIG. 3C HSC-1 (LSK CD150$^+$CD48$^{-/lo}$CD229$^{-/lo}$CD244$^-$). FIG. 3D Fraction I (LSK CD150$^+$CD34$^{-/lo}$CD41$^-$). FIG. 3E CD150$^+$CD48$^-$CD41$^-$ cells, currently used to identify HSCs in situ. Wild-type FMO used to define Hoxb5 negativity for each panel. FIG. 3F Summary percentage of Hoxb5$^+$ and Hoxb5$^-$ negative cells in characterized HSC subfractions. Error bars denote s.d.; n=5 mice (see FIG. 11a-d for gating scheme).

FIG. 4A-4E: LT-HSCs exhibit near-homogenous attachment to VE-cadherin$^+$ cells. FIG. 4A Tissue preparation and representative images of tibial bone marrow plug after paraformaldehyde fixation (day 0) and treatment with reagent-1 (day 7, day 14). FIG. 4B Localization of Hoxb5$^+$ cells (red and arrows) and VE-cadherin$^+$ cells (green) in 3D-reconstructed images. Scale bar, 30 μm. FIG. 4C Representative 2D images of direct (top panel) and non-direct (bottom panel) association of Hoxb5+ cells (red) with VE-cadherin+ cells (green). Scale bar, 10 μm. FIG. 4D Frequency of Hoxb5+ cells (n=287 cells, from n=3 mice) and random spots (n=600 spots, from n=3 mice) plotted against proximity to VE-cadherin+ cells. ***P<0.0001. FIG. 4E Average number of Hoxb5+ cells in proximal, medial, and distal regions of tibia (n=3 mice). NS, not significant. Unpaired Student's t-test (FIG. 4D-4E).

FIG. 5A Ideal expression pattern of HSC-specific genes (pink represents increased expression, blue represents decreased expression). FIG. 5B(i)-(vi) Relative expression of Hoxb5 (FIG. 5B(i), α-catulin/Ctnnal1 (FIG. 5B (ii)), hoxb5 (FIG. 5B (iii)), CD150/Slamf1 (FIG. 5B(iv)), Hoxb4 (FIG. 5B(v)), Gfi-1 (FIG. 5B(vi)) in hematopoietic and stromal populations as determined by microarray analysis.

FIG. 6A Representative flow cytometry gating to isolate pHSCs, MPPs, and oligopotent progenitors from mouse bone marrow. Panels gated as shown after exclusion of doublets and dead cells. FIG. 6B Hoxb5 reporter expression (red) in Flk2+ MPPs, megakaryocyte erythrocyte progenitor (MEP), granulocyte monocyte progenitor (GMP), common myeloid progenitor (CMP), and common lymphoid progenitor (CLP) populations compared to wild-type controls (blue). Values indicate the percentage of mCherry+ cells±s.d. in each fraction for n=3 mice.

FIG. 7: Hoxb5 is not expressed in CD45− bone marrow. Hoxb5 reporter expression in the CD45− compartment within bone marrow of wild-type (red) and three Hoxb5-tri-mCherry mice (blue, orange, and green, n=3 mice).

FIG. 9A-9D: Hoxb5 distinguishes between LT-HSCs and non-LT-HSCs. FIG. 9A Reconstitution kinetics in primary recipients 4, 8, and 12 weeks after receiving ten Hoxb5neg (n=9 mice), Hoxb5lo (n=13 mice), or Hoxb5hi (n=18 mice) pHSCs. Each column represents an individual mouse. FIG. 9B Reconstitution kinetics 4, 8, and 12 weeks after whole bone marrow secondary transplant. FIG. 9C Reconstitution kinetics in primary recipients receiving three Hoxb5neg (n=11 mice), Hoxb5lo (n=12 mice), or Hoxb5hi (n=14 mice) pHSCs. Each column represents an individual mouse. FIG. 9D Reconstitution kinetics following secondary transplant of 100 sorted LSK Hoxb5− (n=14 mice) or Hoxb5+ (n=9 mice) cells and $2 \times 10^5$ supporting cells.

FIG. 11A CD11a− (LSK CD150+ CD34$^{-/lo}$CD11a−) FIG. 11B HSC-1 (LSK CD150+ CD48$^{-/lo}$CD229$^{-/lo}$CD244−). FIG. 11C Fraction I (LSK CD150+CD34$^{-/lo}$CD41−) FIG. 11D CD150+CD48−CD41− cells (n=5 mice).

FIG. 13A-13B Relative frequency of pHSCs (a) and Hoxb5+ LT-HSCs (b) in tibial plugs (flushed) (n=6 mice) compared to tibial plugs plus bones (crushed) (n=6 mice).

FIG. 14A-14C: Hoxb5+ HSCs are evenly distributed in the tibia. FIG. 14A Distribution of Hoxb5+ cells (red and arrows) in bone marrow in 3D-reconstructed images. Nuclei are counterstained with DAPI (blue) wild-type (top panel) Hoxb5-tri-mCherry (middle and bottom panel). Scale bar, 100 μm. FIG. 14B Cartoon representing the location of the proximal, medial, and distal sampling. FIG. 14C Representative 3D-reconstructed images of Hoxb5+ cells (red) in proximal (left column), medial (middle column), and distal (right column) regions of the tibia. Scale bar, 150 μm. Nuclei are counterstained with DAPI (blue); n=3 mice.

DETAILED DESCRIPTION

Figure 1A:
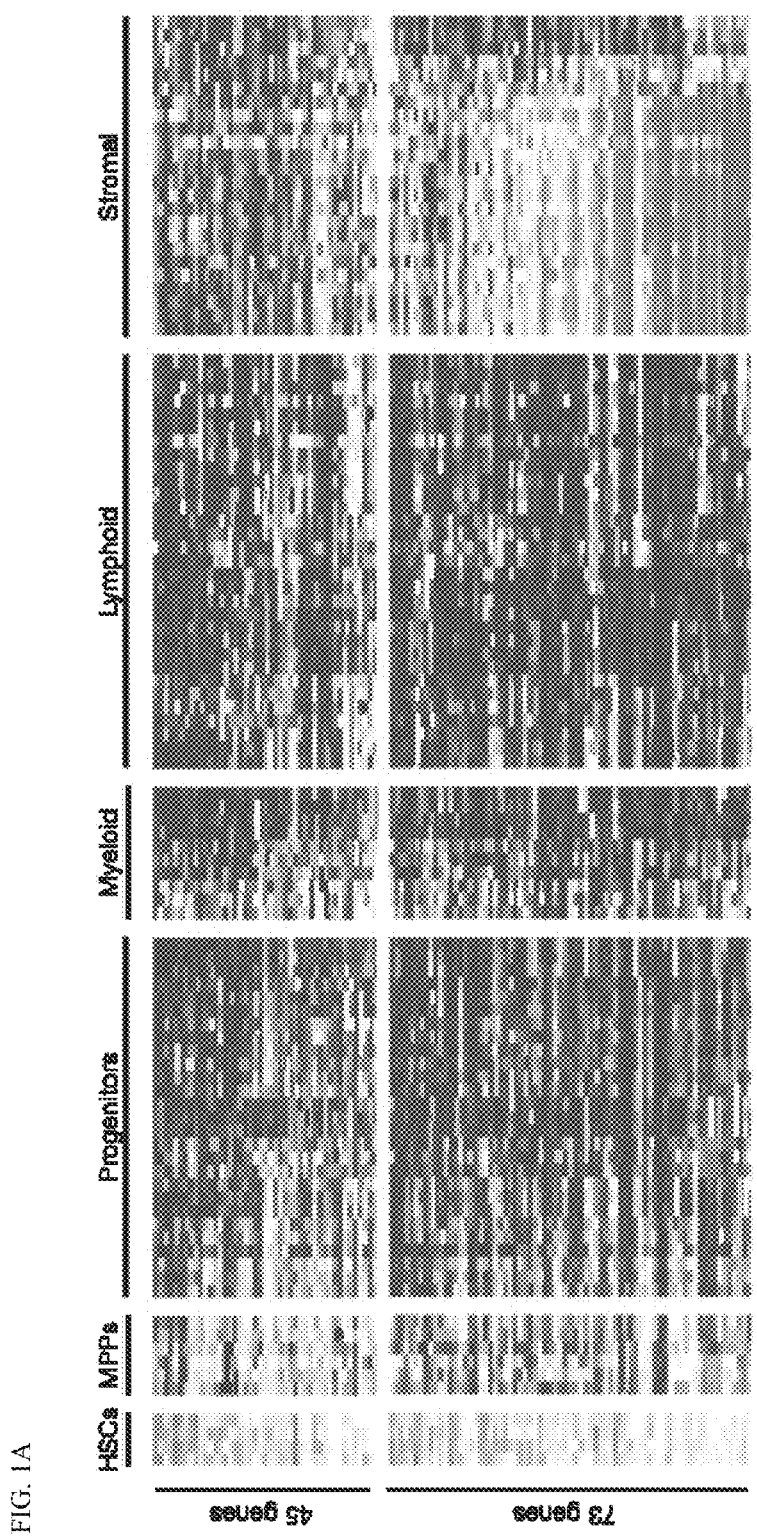

It is demonstrated herein that expression of hoxb5 identifies long-term hematopoietic stem cells. Expression of Hoxb5 distinguishes between LT-HSCs and non-LT-HSCs, and the marker identifies substantially all LT-HSC in the bone marrow. By utilizing fluorescent proteins under the endogenous expression control of Hoxb5, LT-HSC can be monitored and isolated, including without limitation detection and monitoring of HSC in bone morrow; production of LT-HSC from pluripotent stem cells such as iPS cells; for analysis of early stage LT-HSC; in screening methods for expansion and manipulation of LT-HSC, and the like.

Definitions

The term "hematopoietic stem cells," or "HSCs", refers to multipotent cells capable of differentiating into all the cell types of the hematopoietic system, including, but not limited to, granulocytes, monocytes, erythrocytes, megakaryocytes, lymphocytes, dendritic cells; and self-renewal activity, i.e. the ability to divide and generate at least one daughter cell with the identical (e.g., self-renewing) characteristics of the parent cell. Bone marrow has been shown to include at least 3 multipotent populations: Long-Term (LT)-HSC, Short-Term (ST)-HSC, and Multi-Potent Progenitor (MPP, a cell population that has lost the self-renewal capacity of HSC). Rapid and sustained engraftment of syngeneic and even of H2 incompatible allogenic hosts can only be achieved with HSC.

Long term hematopoietic stem cells. A fraction of HSC, which as shown herein is the Hoxb5+ population of cells, are those cells that exhibit long-term reconstitution capacity after transplantation in primary transplant recipients and in secondary recipients. These cells are defined herein as LT-HSC. Only 7-35% of various previously defined immunophenotypic HSCs are LT-HSCs, as shown in the Examples. Previously defined LT-HSC include, for example, CD150+CD34$^{-/lo}$CD11a− cells, CD150+CD48$^{-/lo}$CD229$^{-/lo}$CD244− cells, CD150+CD34$^{-/lo}$CD41− cells; CD150+CD48−CD41− cells; etc.

As used herein, and unless otherwise specified, the term "therapeutically effective amount" of a compound is an amount sufficient to provide a therapeutic benefit in the treatment or management of disease, or to delay or minimize one or more symptoms associated with disease. A therapeutically effective amount of a compound means an amount of therapeutic agent, alone or in combination with other therapies, which provides a therapeutic benefit in the treatment or management of disease. The term "therapeutically effective amount" can encompass an amount that improves overall therapy, reduces or avoids symptoms or causes of disease, or enhances the therapeutic efficacy of another therapeutic agent.

The term "likelihood" generally refers to an increase in the probability of an event. The term "likelihood" when used in reference to the effectiveness of a patient response generally contemplates an increased probability that the symptoms of disease will be lessened or decreased.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

The term "sample" as used herein relates to a material or mixture of materials, typically, although not necessarily, in fluid form, containing one or more components of interest.

"Biological sample" as used herein refers to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to bone marrow, a biological fluid, a blood sample, a urine sample, a skin sample, cell lysate, a cell culture, a cell line, a tissue, an organ, an organelle, and the like. Preferred biological samples include but are not limited to whole blood, partially purified blood, PBMCs, tissue biopsies, and the like.

As used herein, the term "dose amount" refers to the quantity, e.g., milligrams (mg), of the substance which is administered to the subject. In one embodiment, the dose amount is a fixed dose, e.g., is not dependent on the weight of the subject to which the substance is administered. In another embodiment, the dose amount is not a fixed dose, e.g., is dependent on the weight of the subject to which the substance is administered, or for a topical therapy a dose may be related to the surface area that is treated, e.g. dose/m² of skin.

Ranges intermediate to the above-recited ranges are also contemplated by the invention. For example, ranges having any one of these values as the upper or lower limits are also intended to be part of the invention, e.g., about 0.01 mg to about 100 mg, about 1 mg to about 10 mg, etc.

As used herein, the term "periodicity" as it relates to the administration of a substance refers to a (regular) recurring cycle of administering the substance to a subject. In one embodiment, the recurring cycle of administration of the substance to the subject achieves a therapeutic objective. The periodicity of administration of the substance may be about once a week, once every other week, about once every three weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks, about once every 21 weeks, about once every 22 weeks, about once every 23 weeks, about once every 24 weeks, about once every 5-10 days, about once every 10-20 days, about once every 10-50 days, about once every 10-100 days, about once every 10-200 days, about once every 25-35 days, about once every 20-50 days, about once every 20-100 days, about once every 20-200 days, about once every 30-50 days, about once every 30-90 days, about once every 30-100 days, about once every 30-200 days, about once every 50-150 days, about once every 50-200 days, about once every 60-180 days, or about once every 80-100 days. Periodicities intermediate to the above-recited times are also contemplated by the invention. Ranges intermediate to the above-recited ranges are also contemplated by the invention. For example, ranges having any one of these values as the upper or lower limits are also intended to be part of the invention, e.g., about 110 days to about 170 days, about 160 days to about 220 days, etc.

The "duration of a periodicity" refers to a time over which the recurring cycle of administration occurs. For example, a duration of the periodicity of administration of a substance may be may be up to about 4 weeks, up to about 8 weeks, up to about 12 weeks, up to about 16 weeks or more, up to about 20 weeks, up to about 24 weeks, up to about 28 week, up to about 32 weeks or more, during which the periodicity of administration is about once every week. For example, a duration of the periodicity may be about 6 weeks during which the periodicity of administration is about once every 4 weeks, e.g., the substance is administered at week zero and at week four.

As used herein, and unless otherwise specified, the terms "treat," "treating" and "treatment" refer to an action that occurs while a patient is suffering from disease, which reduces the severity of disease, or retards or slows the progression of the disease, or achieving or maintaining a therapeutic objective. An "effective patient response" refers to any increase in the therapeutic benefit to the patient. An "effective patient disease response" can be, for example, a 5%, 10%, 25%, 50%, or 100% decrease in the physical symptoms of disease.

Animals

Transgenic Animals. The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. The transgenic animal may be a mouse, rat, rabbit, etc. In some embodiments the animal is a mouse, which may be any of the many inbred or out bred mouse strains known in the art, e.g. B6, Balb/c, etc., and may be immunocompetent or immunodeficient. Generally the animal will be initially heterozygous, and will be bred to be homozygous.

A transgenic mouse model for analysis of LT-HSC is provided, in which a sequence encoding a marker protein is operably linked to the regulatory sequences that control Hoxb5 expression. Also provided are cells derived from a transgenic mouse, e.g. purified populations of LT-HSC. In some such embodiments the marker sequence is integrated at the chromosomal location of a native Hoxb5 gene. In other embodiments, the regulatory elements that control Hoxb5 expression are isolated and operably joined to a marker coding sequence, e.g. provided on an integrating vector, which vector may include, without limitation, a vector comprising a CRISPR/Cas9 guide sequence for integration at the Hoxb5 site of the chromosome, e.g. at the 5' end of the Hoxb5 coding sequence. Hoxb5 expression can be used as a sole marker for identification and isolation of functionally competent LT-HSCs, and hoxb5 expression is specific to LT-HSC among hematopoietic lineage cells.

To provide for LT-HSC specific expression, sequences encoding the marker are preferably transcribed by the endogenous Hoxb5 promoter regulation. The sequence encoding the marker may be, for example, expressed in tandem with Hoxb5 when separated by an internal ribosome entry site, (IRES); when separated by a peptide cleavage site, e.g. P2A self-cleaving peptide, and the like.

Marker sequence include sequences encoding molecules that can easily be detected by persons of ordinary skill in the art, such as unique cell surface molecules. Markers of interest include, for example, fluorescent proteins or enhanced forms thereof; any cell surface protein marker or ligand that is not normally not expressed by a cell in the transgenic animal, for example, a cell surface molecule found in a different species such as truncated forms of human CD2 or human CD25, enabling their detection with mAbs; enzymes, such as β-lactamase, chloramphenicol acetyltransferase, adenosine deaminase, aminoglycoside phosphotransferase, dihydrofolate reductase, thymidine kinase, luciferase or xanthine guanine phosphoribosyltransferase polypeptide; or small peptide tags such as a c-myc peptide, a polyhistidine, a FLAG epitope, etc. Expression of a reporter molecule can be detected using the appropriate instrumentation or reagent, for example, by detecting fluorescence of a fluorescent reporter protein or, for example, light emission upon addition of luciferin to a luciferase reporter molecule, or by detecting binding of nickel ion to a polypeptide containing a polyhistidine tag.

In some embodiments the marker protein is an optically detectable protein. The marker sequence may be a protein detectable by luminescent or fluorescent properties, including without limitation luciferase and variants thereof; *Aequorea victoria* sourced fluorescent proteins and derivatives there, including without limitation Blue-Fluorescent Protein (BFP), Cyan-Fluorescent Protein (CFP), green fluorescent protein (GFP), enhanced GFP with red-shifted excitation (EGFP), enhanced Yellow-Fluorescent Protein (EYFP), photoactivatable green fluorescent protein (PA-GFP), etc., *Discoma* species fluorescent protein, e.g. dsRed, mFruits, mCherry, etc.; TagRFPs; *Entacmaea quadricolor* fluorescent protein, e.g. eqFP611; Dronpa; EosFP; and the like as known in the art. Such fluorescent and bioluminescent protein are known in the art, for example see any of U.S. Pat. Nos. 7,166,444; 7,338,784; 7,442,521; 7,537,915; 7,442,522; 7,338,782; 7,338,783; 7,338,785; 7,344,862; and 8,012,682.

As an alternative to a directly detectable marker such as a fluorescent or luminescent protein, a marker may be any protein that does not interfere with the biology of the cell and that provides a unique sequence can be used as a marker, e.g. a cell surface protein to which antibody reagents are available, and the like.

Transgenic animals of the invention generally comprise an exogenous nucleic acid sequence present as an extrachromosomal element or more usually stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

Transgenic animals fall into two groups, colloquially termed "knockouts" and "knockins". In the present invention, knockin animals comprise a marker protein under regulatory control of hoxb5 regulatory sequences, and preferably integrated at the chromosomal location of Hx5b. By "operably linked" is meant that a DNA sequence and a regulatory sequence(s) are connected in such a way as to permit gene expression when the appropriate molecules, e.g. transcriptional activator proteins, are bound to the regulatory sequence(s).

Transgenic mice may be generated by injection of the DNA construct into the pronucleus of fertilized oocytes. The transgenic animals and xenografted animals may be used in a wide variety of ways, e.g. in gene discovery; for dissection of HSC growth regulation; for screening assays; and the like.

In some embodiments, a biological sample comprising LT-HSC isolated from a transgenic mouse described herein is provided. A sample may be obtained from, for example, peripheral blood, thymus, bone marrow, fetal liver, etc. Cells may be isolated from the biological sample, for example by flow cytometry, immunoselection techniques, such as high-throughput cell sorting using flow cytometric methods, affinity methods with antibodies labeled to magnetic beads, such as magnetic-activated cell separation (MACS), biodegradable beads, non-biodegradable beads, antibodies panned to surfaces, including dishes, automated single-cell sorting using dual-beam optical trapping, differential adhesion cell sorting, and micro-fabricated fluorescence-activated cell sorting, and any combination of such methods to obtain a population of Hoxb5+ LT-HSC. The population of cells may be grown in culture, e.g. expanded, grown in an artificial niche, exposed to factors of interest, etc.

Cells isolated from the transgenic animal may include hematopoietic cell populations, e.g. bone marrow, peripheral blood, umbilical cord blood, spleen, fetal liver, and the like. Hematopoietic stem and progenitor cells may be isolated from such populations. Cells derived from the transgenic animal may include pluripotent stem cells, e.g. embryonic stem cells, induced pluripotent stem cells, etc., which cells can be differentiated to hematopoietic stem and progenitor cells.

The terms "isolate" and "methods of isolation," as used herein, refer to any process whereby a cell or population of cells, such as a population of LT-HSC, is purified from a complex population. The term "isolated population," refers to a population of cells, e.g. LT-HSC that has been separated from a biological sample or from an in vitro culture derived therefrom.

Cell surface markers previously identified as relevant to identification of HSC and LT-HSC may be used to further define, confirm, track differentiation, etc. of the LT-HSC population. Markers may be proteins, particularly cell surface proteins, lipids, polysaccharides, nucleic acids etc. Examples of morphological characteristics or traits include, but are not limited to, cellular shape, cellular size, cellular appearance (e.g., smooth, translucent), and cellular nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages.

A cell can be designated "positive" or "negative" for any given cell-surface marker. A cell is considered "positive" for a cell-surface marker if it expresses the marker on its cell-surface in amounts sufficient to be detected using methods known to those of skill in the art, such as contacting a cell with an antibody that binds specifically to that marker, and subsequently performing flow cytometric analysis of such a contacted cell to determine whether the antibody is bound the cell. Methods known to those of skill in the art include contacting a cell with an antibody that binds specifically to that marker and subsequently performing flow cytometric analysis of such a contacted cell to determine whether the antibody is bound the cell.

Screening Assays

The animals and cells derived therefrom may be used for screening candidate therapies modifiers, i.e. compounds and factors that affect LT-HSC. A wide variety of assays may be used for this purpose, including immunoassays for protein binding; determination of cell growth, differentiation and functional activity; disease phenotypes of the bone marrow, and the like.

Typically the candidate compound will be added to LT-HSC cells and/or transgenic animal, and the response of the cells monitored through evaluation of cell surface phenotype, functional activity, patterns of gene expression, and the like. Through use of the subject transgenic animals or cells derived therefrom, one can identify ligands or substrates that act on stem cell quiescence, long term maintenance of a stem cell phenotype, initiation of cell cycle and differentiation, and the like. Depending on the particular assay, whole animals may be used, or cell derived therefrom. Cells may be freshly isolated from an animal, or may be immortalized in culture.

The term "agent" as used herein describes any molecule, e.g. protein or pharmaceutical, with the capability of affecting the biological action of LT-HSC. Generally a plurality of assay mixtures are run in parallel with different agent concentrations to obtain a differential response to the various concentrations. Typically, one of these concentrations serves as a negative control, i.e. at zero concentration or below the level of detection. Screening may be directed to known pharmacologically active compounds and chemical analogs thereof.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4 and 40.degree. C. Incubation periods are selected for optimum activity, but may also be optimized to facilitate rapid high-throughput screening. Typically between 0.1 and 1 hours will be sufficient.

For example, detection may utilize staining of cells or histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

Gene expression in the cells of the invention may be assessed following a candidate treatment or experimental manipulation. The expressed set of genes may be compared with a variety of cells of interest, e.g. keratinocytes, etc., as known in the art. Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+ mRNA. One of skill in the art can readily use these methods to determine differences in the size or amount of mRNA transcripts between two samples. For example, the level of particular mRNAs in mast cells is compared with the expression of the mRNAs in a reference sample.

In another screening method, the test sample is assayed at the protein level. Methods of analysis may include 2-dimensional gels; mass spectroscopy; analysis of specific cell fraction, e.g. lysosomes; and other proteomics approaches. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

Where an animal is being tested, the bone marrow, circulating blood cells, etc. may be analyzed.

Parameters of interest refers to measureable components or qualities of LT-HSGs, particularly components that can be accurately measured, most desirably in a high-throughput system. A cellular parameter can be any measurable parameter related to a phenotype, function, or behavior of a cell. Such cellular parameters include, changes in characteristics and markers of a LT-HSC, including but not limited to changes in viability, cell growth, expression of one or more or a combination of markers, such as cell surface determinants, such as receptors, proteins, including conformational or posttranslational modification thereof, lipids, carbohydrates, organic or inorganic molecules, nucleic adds, e.g. mRNA, DNA, global gene expression patterns, etc. Such cellular parameters can be measured using any of a variety of assays known to one of skill in the art. For example, viability and cell growth can be measured by assays such as Trypan blue exclusion, CFSE dilution, and $^3$H incorporation. Expression of protein markers can be measured, for example, using flow cytometric assays, Western blot techniques, or microscopy methods. Gene expression profiles can be assayed, for example, using microarray methodologies and quantitative or semi-quantitative real-time PCR assays.

While most cellular parameters will provide a quantitative readout, in some instances a semi-quantitative or qualitative result can be acceptable. Readouts can include a single determined value, or can include mean, median value or the variance, etc. Characteristically a range of parameter readout values can be obtained for each parameter from a multiplicity of the same assays. Variability is expected and a range of values for each of the set of test parameters will be obtained using standard statistical methods with a common statistical method used to provide single values.

Functional aspects of LT-FSCs phenotypes, such as the ability to give rise to long-term, multi-lineage reconstitution in a recipient or a secondary recipient, can be easily determined by one of skill in the art using routine methods known in the art, and as described herein, for example, in the Examples.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular. Other than in the operating examples, or where otherwise indicated, all numbers expressing quantities of ingredients or reaction conditions used herein should be understood as modified in all instances by the term "about." The term "about" when used in connection with percentages can mean±1%.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

EXPERIMENTAL

Example 1

Hoxb5 Marks Long-Term Hematopoietic Stem Cells and Reveals a Homogenous Perivascular Niche Hematopoietic stem cells (HSCs) are arguably the most extensively characterized tissue stem cells. Since the identification of HSCs by prospective isolation, complex multi-parameter flow cytometric isolation of phenotypic subsets has facilitated studies on many aspects of HSC biology, including self-renewal, differentiation, ageing, niche, and diversity. Here we demonstrate by unbiased multi-step screening, identification of a single gene, homeobox B5 (Hoxb5, also known as Hox-2.1), with expression in the bone marrow that is limited to long-term (LT)-HSCs in mice. Using a mouse single-colour tri-mCherry reporter driven by endogenous Hoxb5 regulation, we show that only the Hoxb5$^+$ HSCs exhibit long-term reconstitution capacity after transplantation in primary transplant recipients and, notably, in secondary recipients. Only 7-35% of various previously defined immunophenotypic HSCs are LT-HSCs. Finally, by in situ imaging of mouse bone marrow, we show that>94% of LT-HSCs (Hoxb5$^+$) are directly attached to VE-cadherin$^+$ cells, implicating the perivascular space as a near-homogenous location of LT-HSCs.

Prospective isolation of HSCs requires that the isolated cells are capable of long-term production of all blood cell types in primary irradiated hosts, as well as self-renewal, such that the cells can be transplanted to secondary hosts to give rise to long-term multilineage repopulation. From the first enrichment and isolation of candidate HSCs, this activity has been entirely contained in cell-surface-marker-defined cell populations, and more recently in fluorescent reporters. However, the precise fraction of cells in those populations that are true LT-HSCs remains unknown.

Figure 1B:
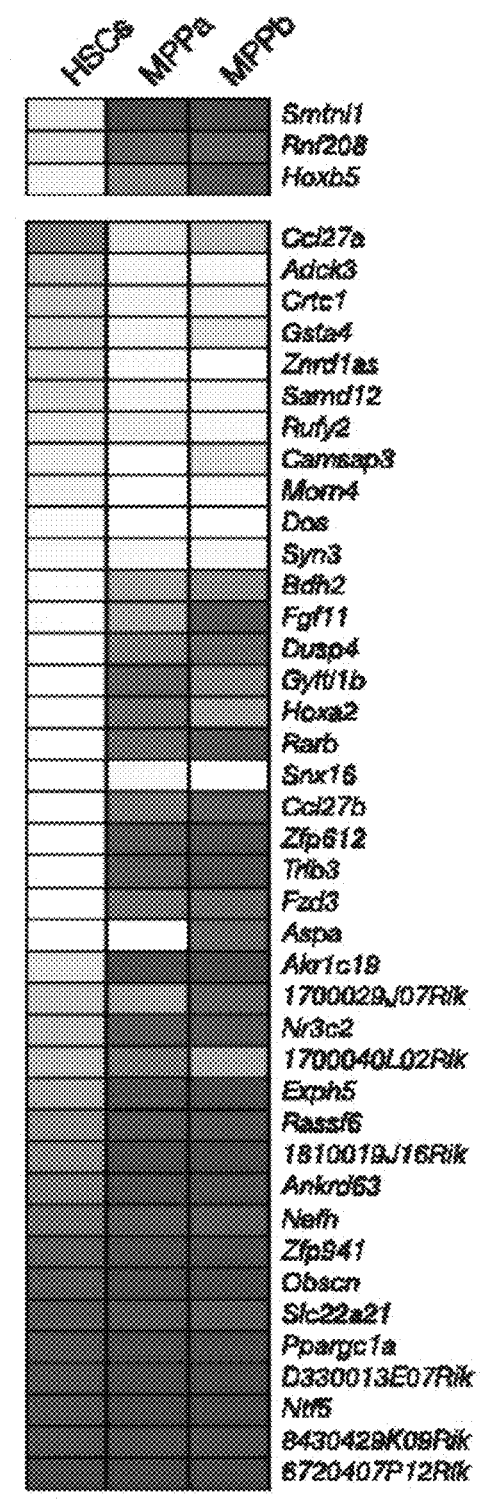
Figure 1C:
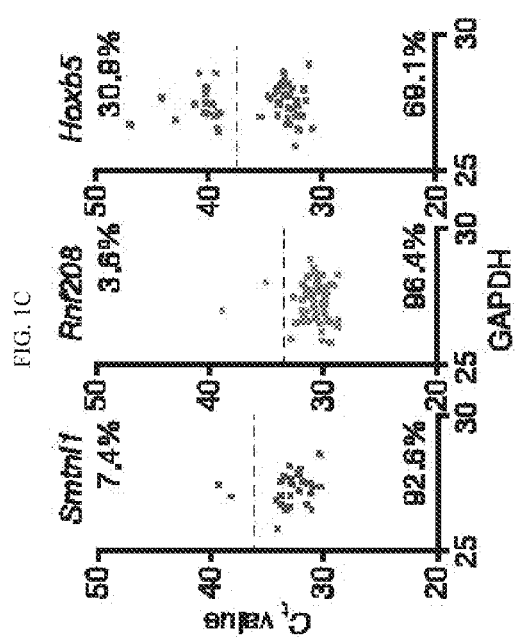
Figure 1D:
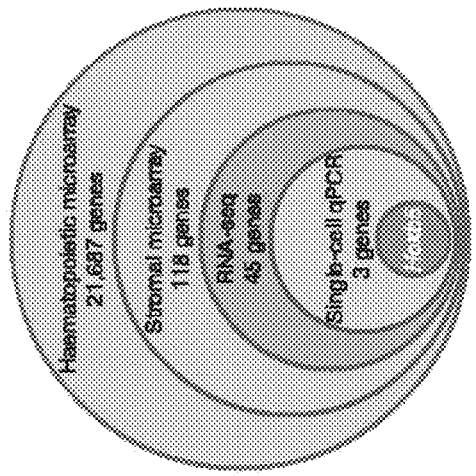

To enable further purification of LT-HSCs, we sought to identify genes expressed exclusively in HSCs within cell populations resident in mouse bone marrow, detectable by flow cytometry and in situ fluorescence, and thus performed the following four-step screening (FIG. 1d).

Figure 5A:
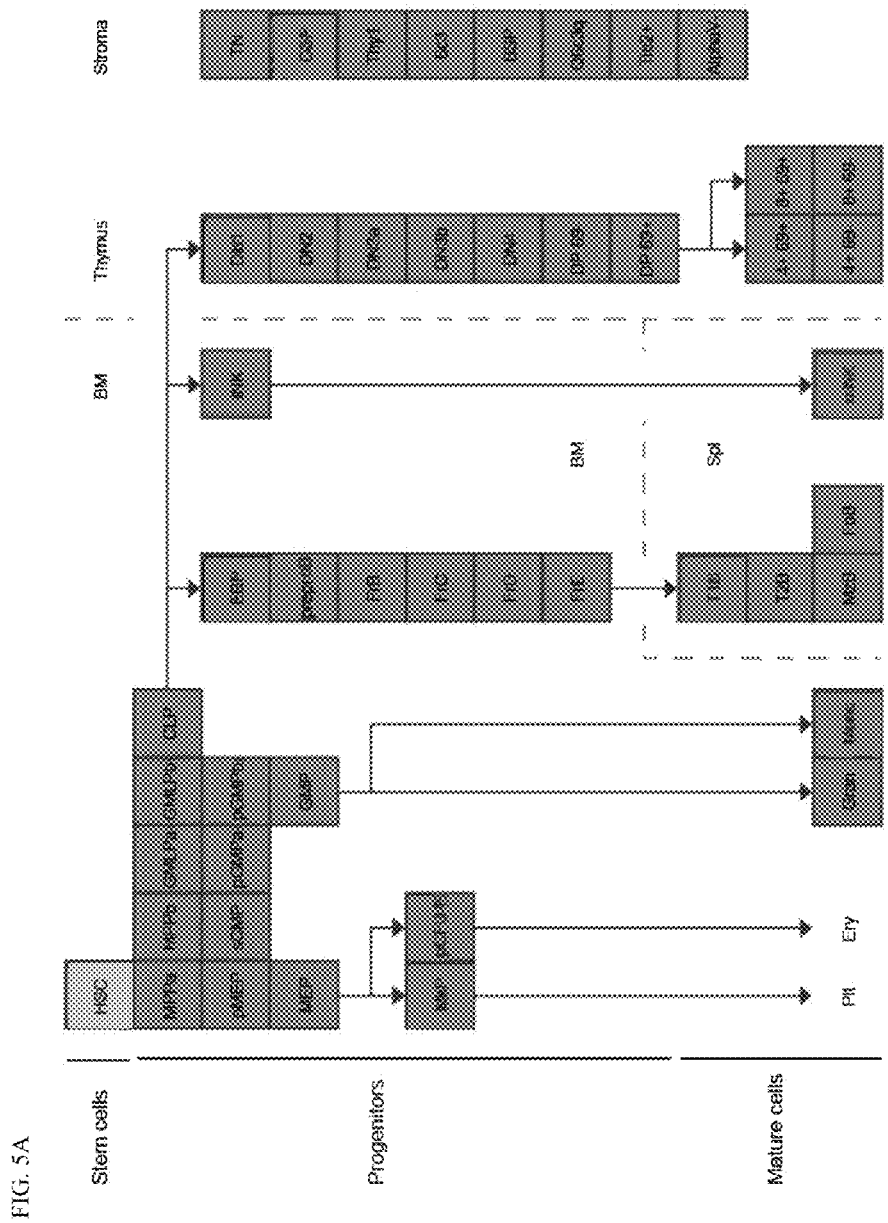
FIG. 5A-5B(i)-(vi): GEXC expression of previously reported HSC markers in mouse bone marrow.
Figure 5B:
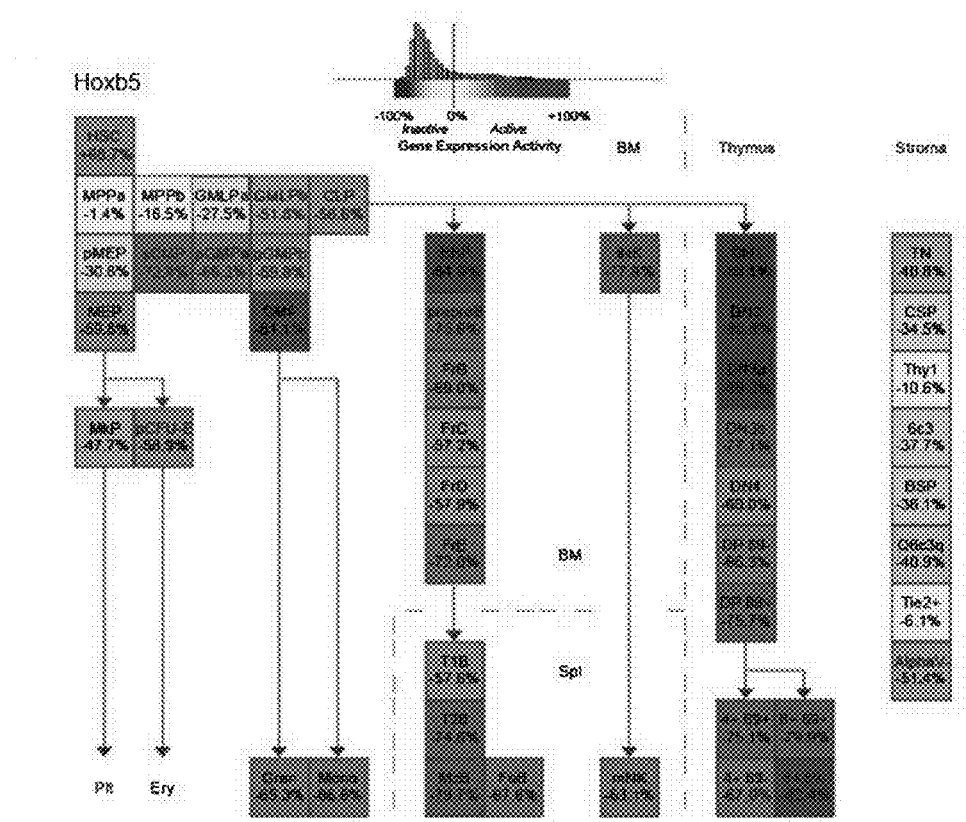
Figure 5B:
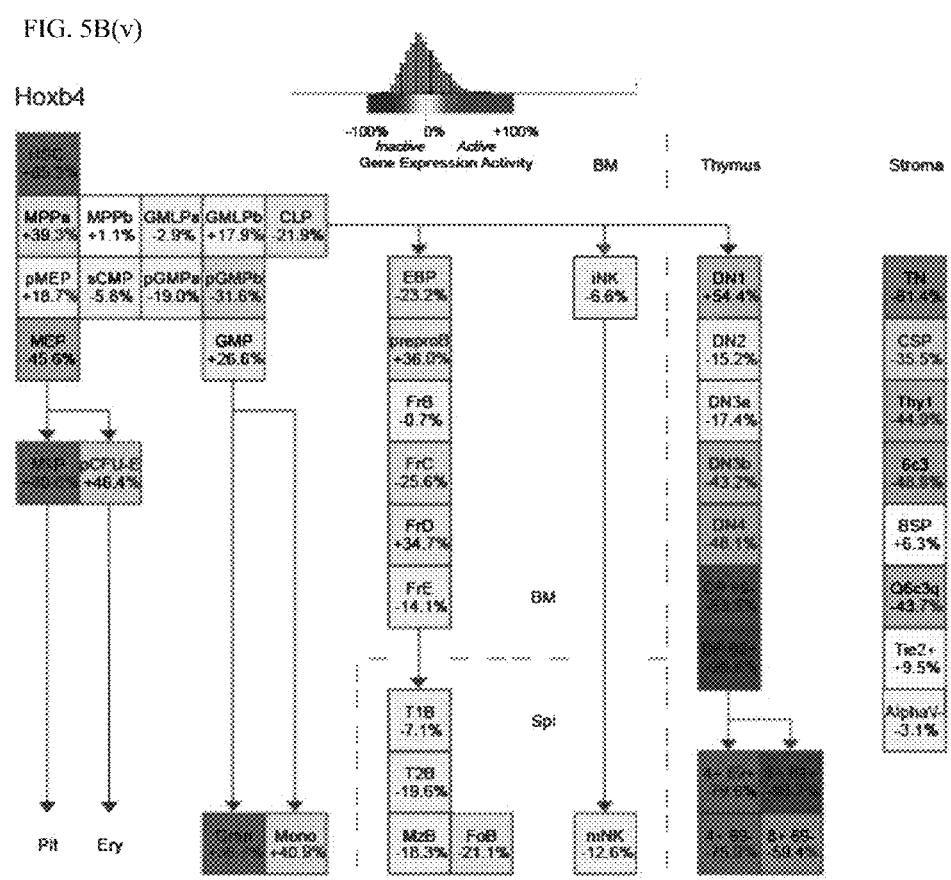

First, we compared microarray gene expression assays among 28 distinct populations of the hematopoietic system (FIG. 5a). Using the Gene Expression Commons platform, we identified 118 candidate HSC-specific genes (FIG. 1a). Surprisingly, this list did not include all previously reported HSC-specific markers (FIG. 5b). Second, to identify HSCs in situ, we excluded candidates that also label non-hematopoietic cells present in the bone marrow such as stromal and endothelial cells. Consequently, we excluded genes expressed in eight distinct non-hematopoietic bone marrow populations, thereby narrowing the list to 45 candidate genes (FIG. 1a).

Next, to ensure that the expression of any candidates could be detected by both flow cytometry and in situ fluorescence, we used RNA-sequencing (RNA-seq) combined with a threshold gene standard to estimate the fragments per kilobase of transcript per million mapped reads (FPKM) value that could serve as a detection threshold. From the bone marrow of 12-week-old mice, we sorted and RNA-sequenced immunophenotypically defined (Lin$^-$c-Kit$^+$Sca-1$^+$CD150$^+$CD34$^{-/lo}$Flk2$^-$) HSCs (hereafter referred to as pHSCs), multipotent progenitors subset A (MPPa; Lin$^-$c-Kit$^+$Sca-1$^+$CD150$^+$CD34$^+$Flk2$^-$), and multipotent progenitors subset B (MPPb; Lin$^-$c-Kit$^+$Sca-1$^+$CD150$^-$ CD34$^+$Flk2$^-$) (FIG. 1b) to determine the FPKM value of candidate genes. On the basis of Bmi-1-eGFP knock-in reporter expression, we found that a single copy of eGFP is detectable at an estimated FPKM value of ~20. However, this high threshold would have excluded all candidate genes. Therefore, we designed a targeting construct (FIG. 1e) with three copies of mCherry, bringing the theoretical detection limit to ~7 FPKM. Lastly, to minimize aberrant detection, we set threshold FPKM values for both the MPPa and MPPb fractions to 2.5. Only three genes, Hoxb5, Rnf208, and Smtnl1, met these criteria (FIG. 1b).

Given previous reports of heterogeneity within pHSCs, we analysed single cells to determine whether the remaining candidate genes were heterogenously expressed among pHSCs. We reasoned that an ideal pan-HSC candidate gene would label the majority of pHSCs, with quantitative differences potentially reflecting HSC heterogeneity/diversity. We thus performed single-cell quantitative PCR (qPCR) analysis of pHSCs, and evaluated expression of Hoxb5, Rnf208, and Smtnl1. Only Hoxb5 exhibited bimodal expression, in comparison to the unimodality of Rnf208 and Smtnl1 (FIG. 1c). Therefore, from the entire HSC transcriptome, only Hoxb5 satisfied the criteria of our extensive unbiased screening (FIG. 1d).

Figure 1E:
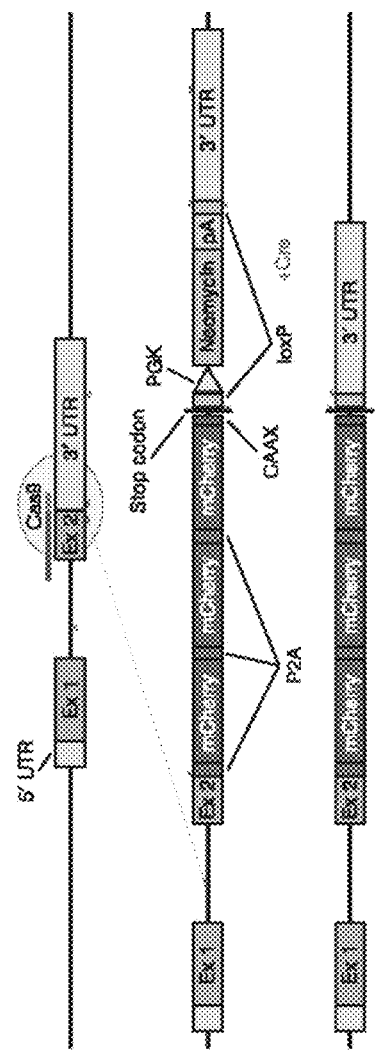

We next sought to generate a Hoxb5 reporter with minimal disruption of endogenous Hoxb5 function. Thus we designed our targeting construct and CRISPR guide sequences to facilitate an in-frame knock-in to the endogenous Hoxb5 gene locus immediately 5' of the only endogenous stop codon. We used three tandem mCherry cassettes separated by porcine teschovirus-1 2A (P2A) sequences, with the terminal mCherry carrying a CAAX membrane localization sequence (Hoxb5-tri-mCherry) (FIG. 1e).

Figure 1F:
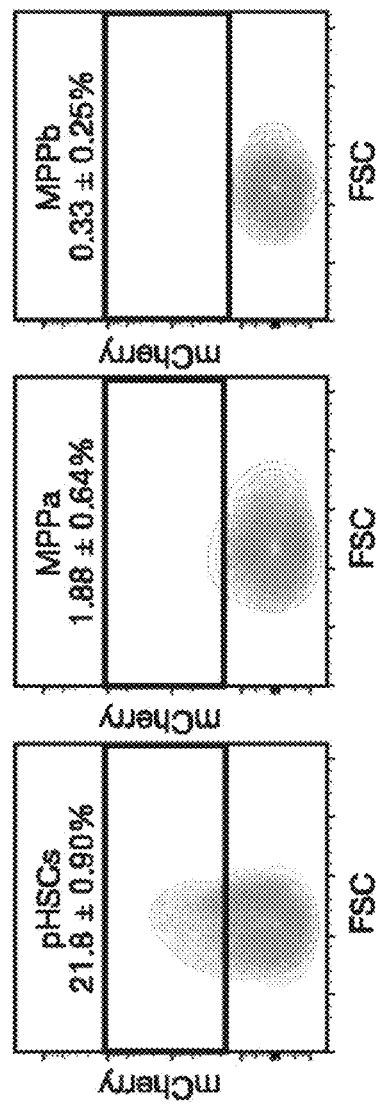
Figures 6A, 6B:
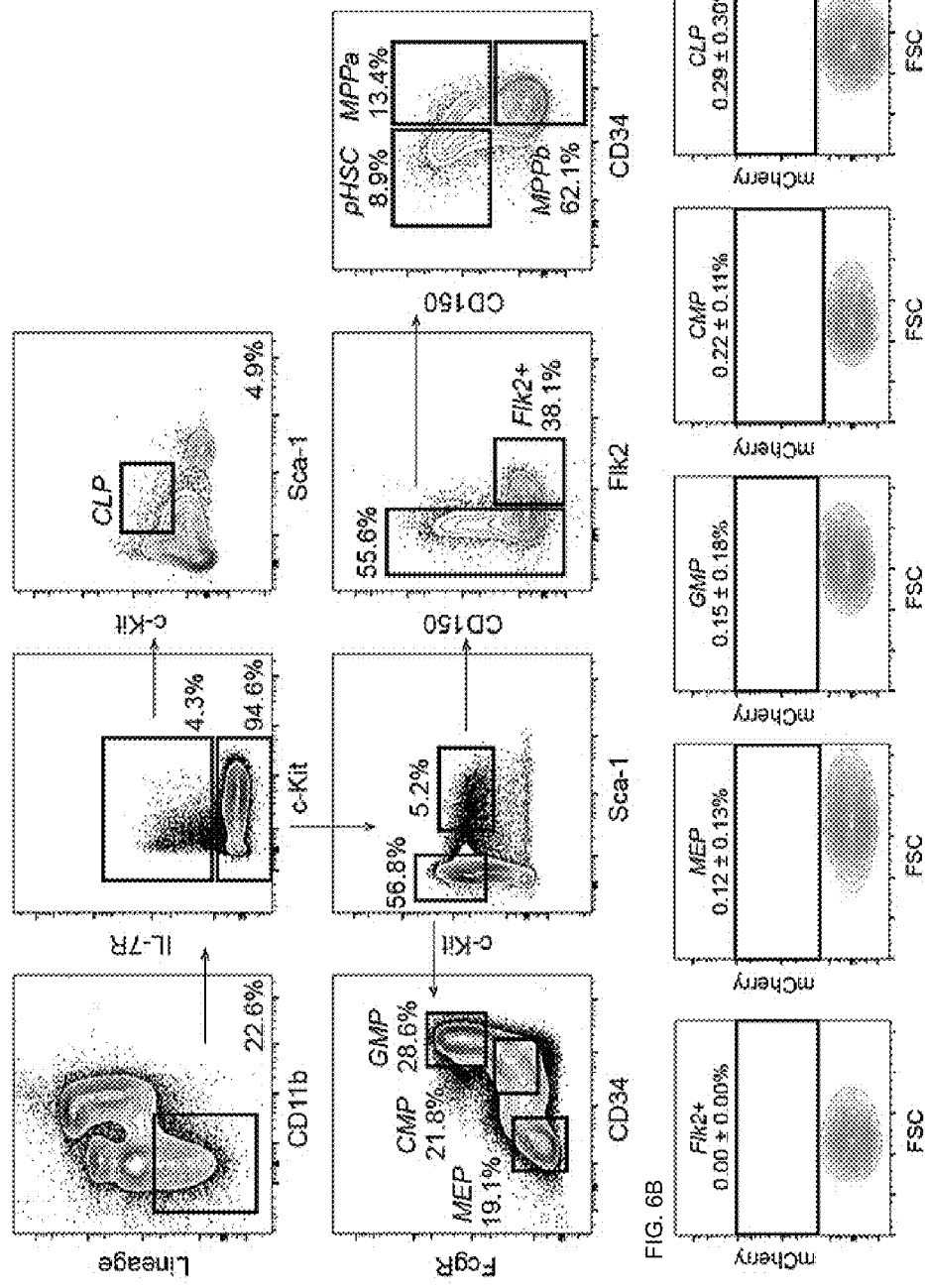
FIG. 6A-6B: Gating scheme for HSC and progenitors.
Figure 8:
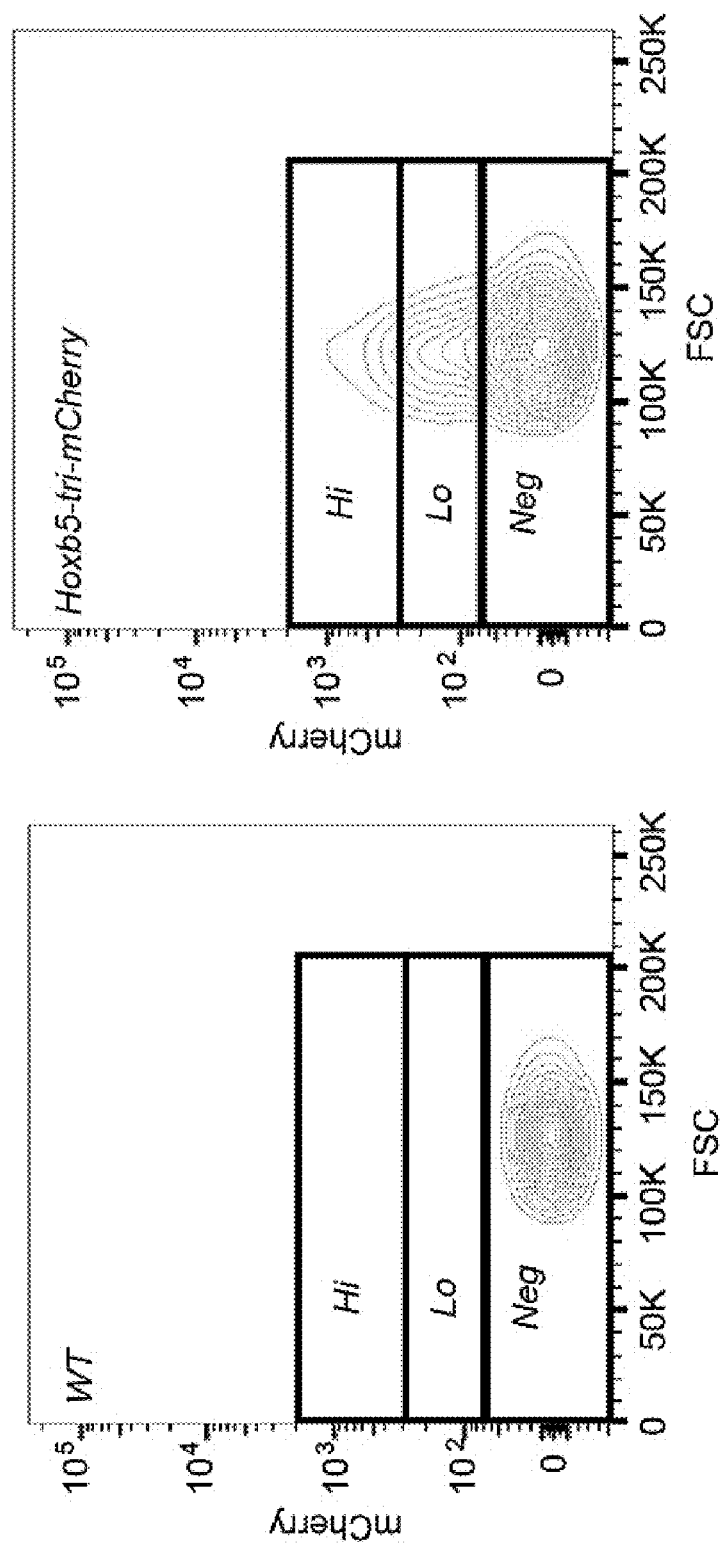
FIG. 8: FMO gating for Hoxb5+ signal. Representative flow cytometry gating to separate mCherry (Hoxb5)-high, -low, and -negative populations in both wild-type and Hoxb5-tri-mCherry mice.

To evaluate the specificity of this reporter, we isolated whole bone marrow cells from 12-week-old reporter mice and measured mCherry$^+$ cells in the following immunophenotypic populations: pHSC, MPPa, MPPb, Flk2$^+$ multipotent progenitor, megakaryocyte erythrocyte progenitor, granulocyte monocyte progenitor, common myeloid progenitor, common lymphoid progenitor fractions; differentiated cell populations (B cell, T cell, natural killer (NK) cell, neutrophil, eosinophil, monocyte, macrophage, dendritic cell, red blood cell, and megakaryocyte); and in CD45– stromal fractions (FIG. 1f, FIG. 6a, b, FIG. 7). Consistent with our initial screen (FIG. 1a-d), and using wild-type mice as a fluorescence minus one (FMO) threshold, mCherry-labelled cells were highly enriched in the pHSC fraction (21.8%±0.90%), had a low frequency in the MPPa fraction (1.88%±0.64%), and background frequencies in the remaining fractions (FIG. 1f, FIGS. 6b and 7). Interestingly, as only a minority of pHSCs were mCherry$^+$, this suggested that either our reporter labelled only a subfraction of HSCs or only a subfraction of pHSCs were indeed HSCs.

To distinguish between these two possibilities and to determine whether Hoxb5 is a reporter of LT-HSCs, we characterized Hoxb5-expressing cells by transplantation. In order to be inclusive of all events in the pHSC gate, we used wild-type FMO to define Hoxb5 negativity (Hoxb5neg or sometimes referred to as Hox5–) and divided the positive fraction (sometimes referred to as Hox5+) into Hoxb5hi (top 5th percentile) and Hoxb5lo (14.1±7.7%). Ten-cell and three-cell grafts of Hoxb5$^{hi}$, Hoxb5$^{lo}$, or Hoxb5$^{neg}$ pHSCs were transplanted with supporting bone marrow cells into irradiated mouse recipients. We used CD45.2 expression to assess donor HSC contribution to hematopoietic lineages at 4-week intervals (FIG. 2a). Analysis of peripheral blood 16 weeks after transplantation of ten cells demonstrated that multilineage reconstitution was present in 78% of Hoxb5hi, 70% of Hoxb5lo, and 44% Hoxb5neg pHSC recipients (FIG. 2b). Three-cell transplants exhibited similar kinetics (FIG. 5c). Notably, the chimaerism of the Hoxb5neg pHSCs decreased over time, in particular between 4 to 8 weeks and shifted towards a predominantly lymphoid chimaerism (FIG. 2b, d), suggesting that either the Hoxb5neg fraction comprised of lymphoid-biased HSCs or, more likely, transiently self-renewing short-term (ST)-HSCs and/or MPPs that had given rise to long-lived lymphocytes. FIG. 2: Hoxb5 distinguishes between LT-HSC and non-LT-HSC.

Figure 9B:
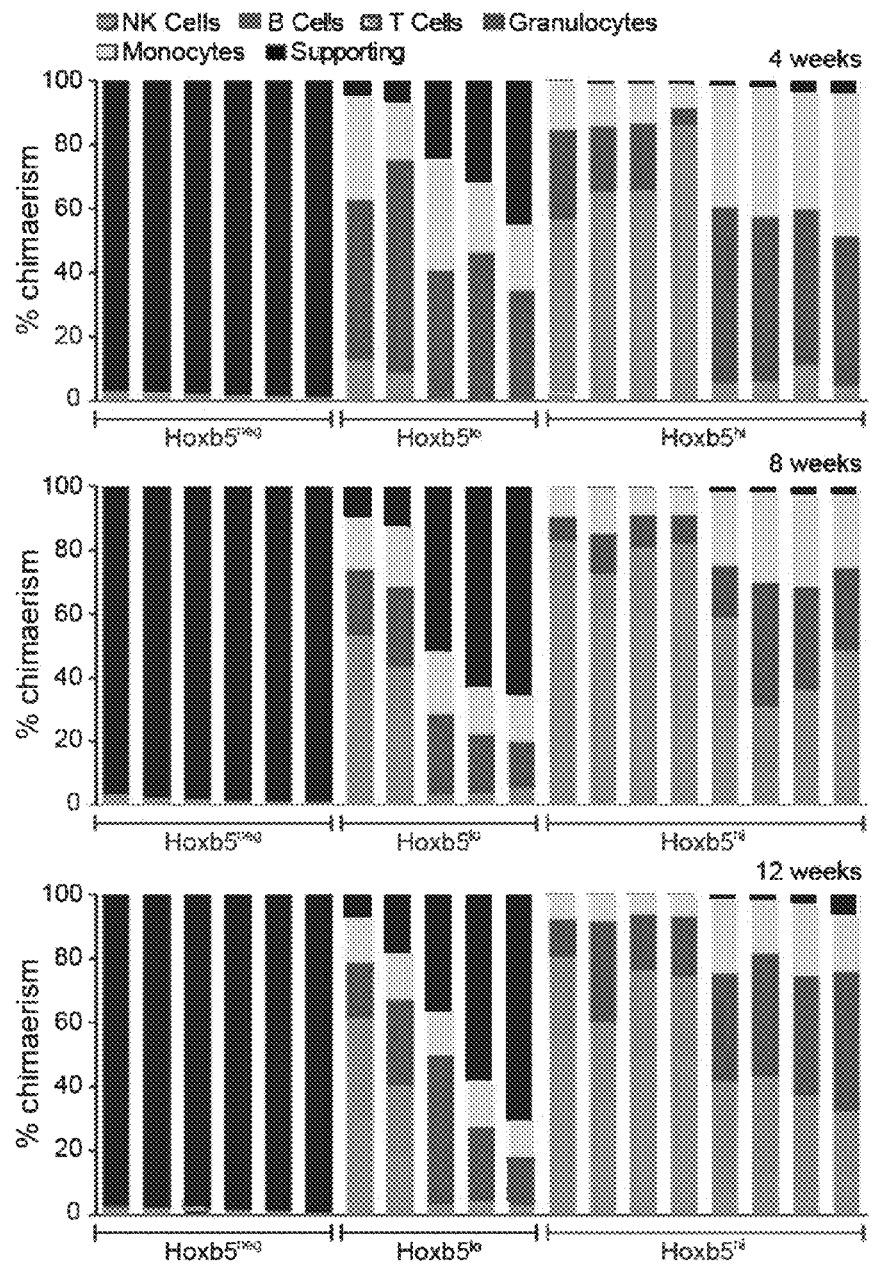
Figure 9C:
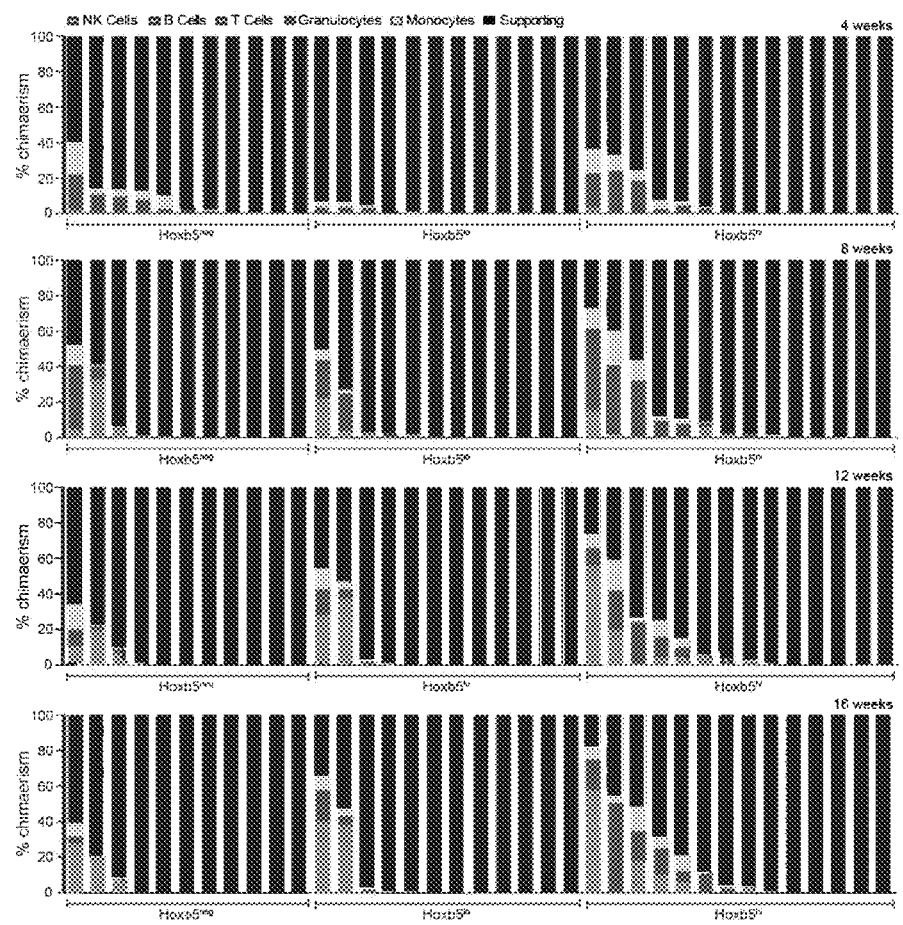
Figure 9D:
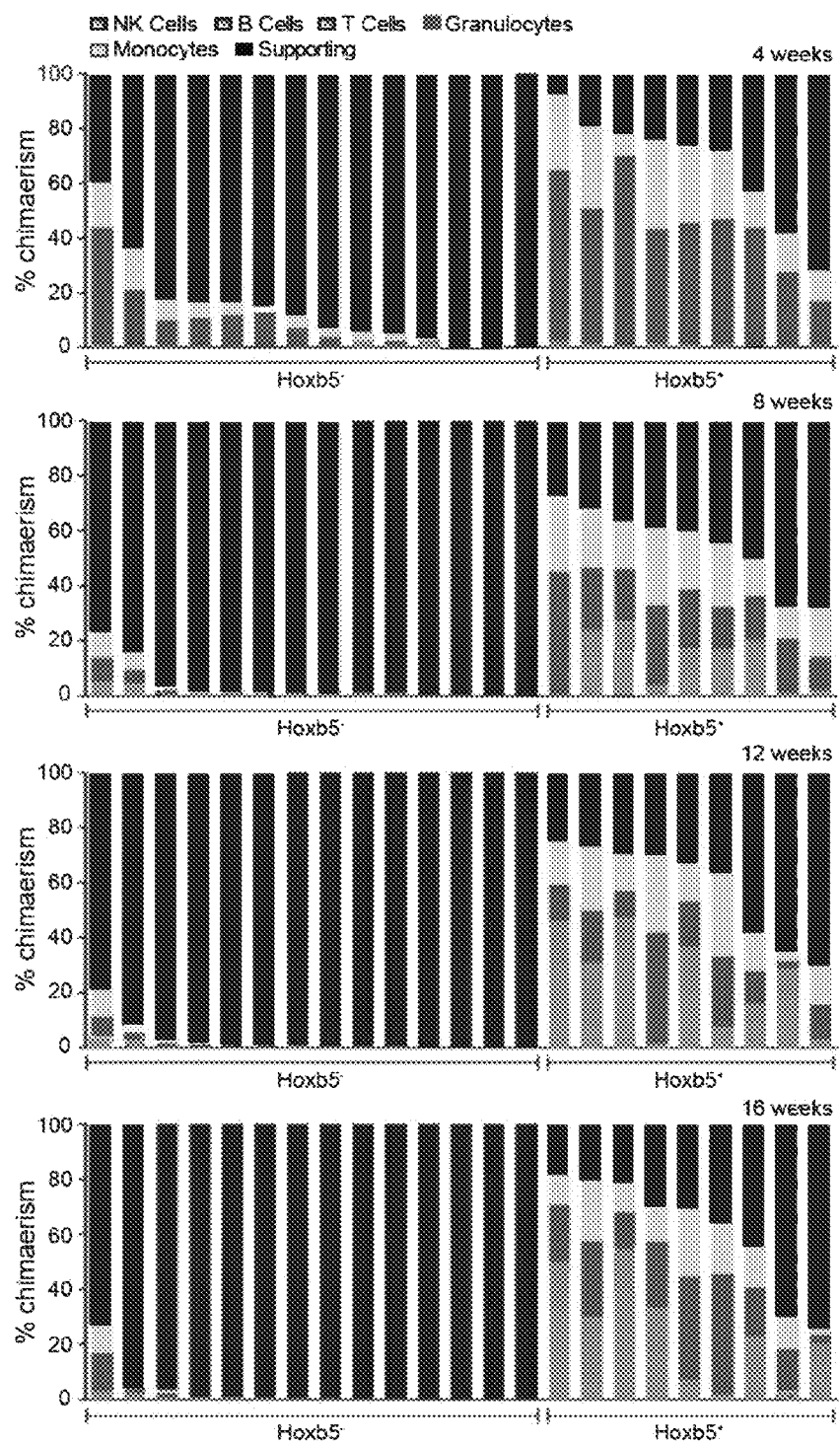
Figure 10:
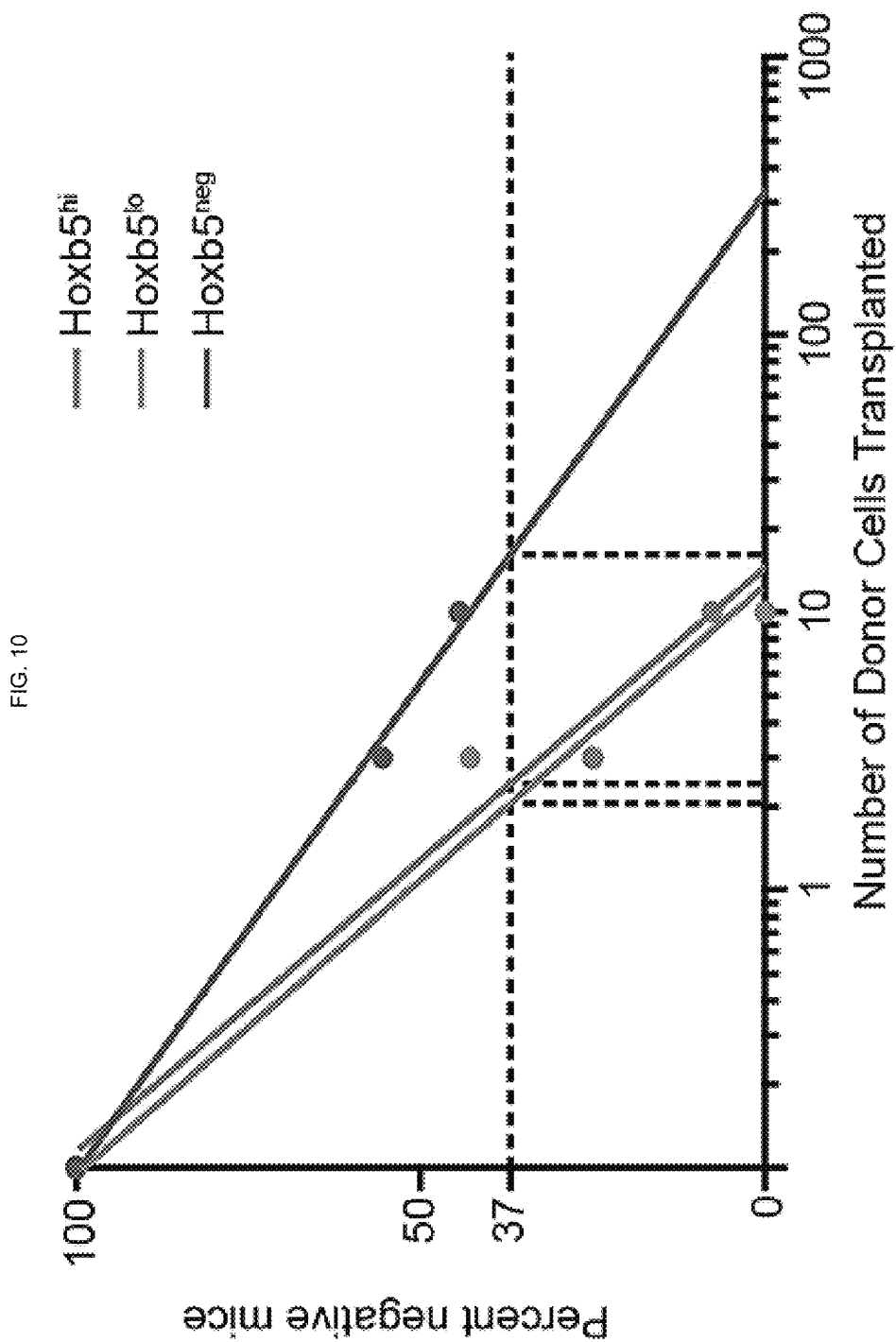
FIG. 10: Limiting dilution analysis of Hoxb5+ and Hoxb5− pHSCs. Limiting dilution results of ten- and three-cell transplants of Hoxb5hi (red, n=18 mice for ten-cell and n=14 mice for three-cell), Hoxb5lo (green, n=13 mice for ten-cell and n=12 mice for three-cell), and Hoxb5neg (blue, n=9 mice for ten-cell and n=11 mice for three-cell). Frequency of LT/ST-HSCs by limiting dilution analysis is 1 in 2.1 for Hoxb5hi, 1 in 2.4 for Hoxb5lo, and 1 in 16.1 for Hoxb5neg cells.
Figure 11A:
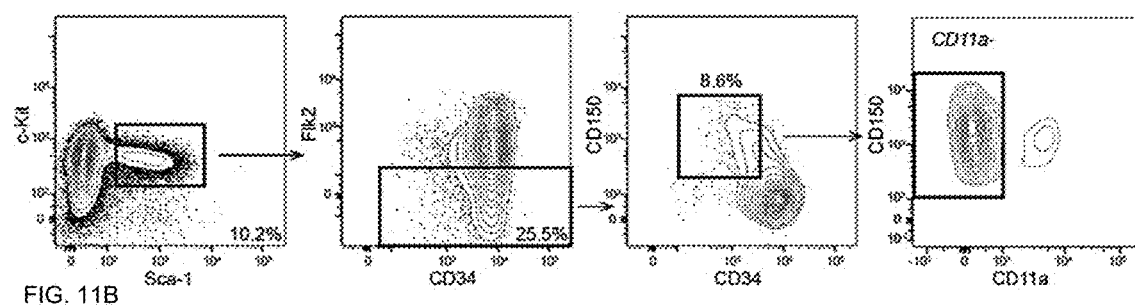
FIG. 11A-11D: Previously defined HSC immunophenotypes contain Hoxb5− cells. Representative HSC gating strategy for various HSC definitions after exclusion of doublets and dead cells.
Figure 11B:
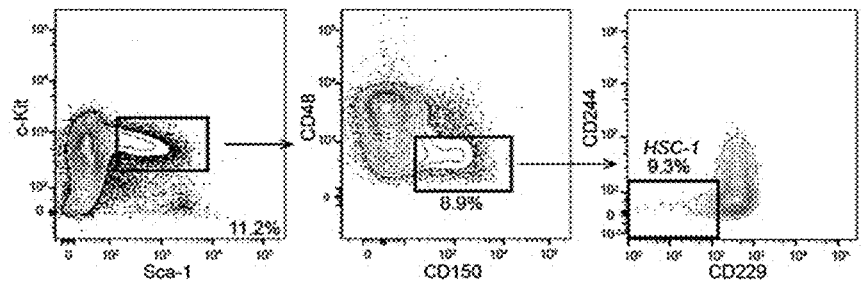
Figure 11C:
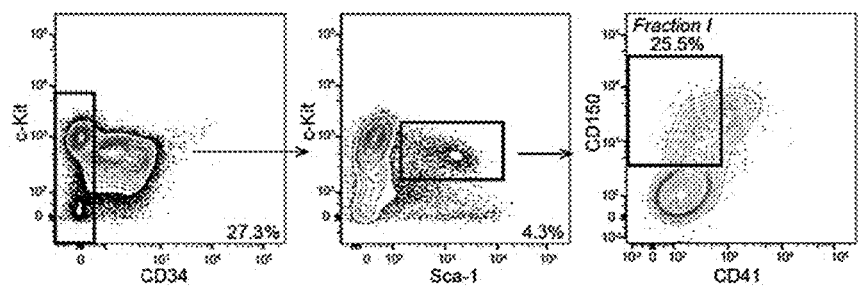
Figure 11D:
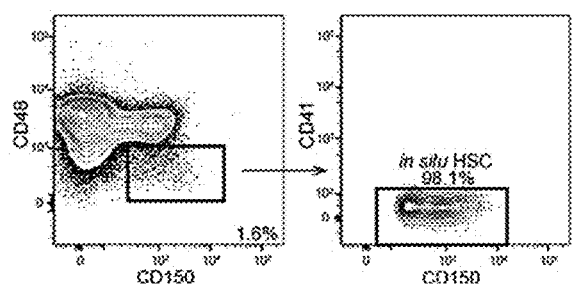
Figure 12:
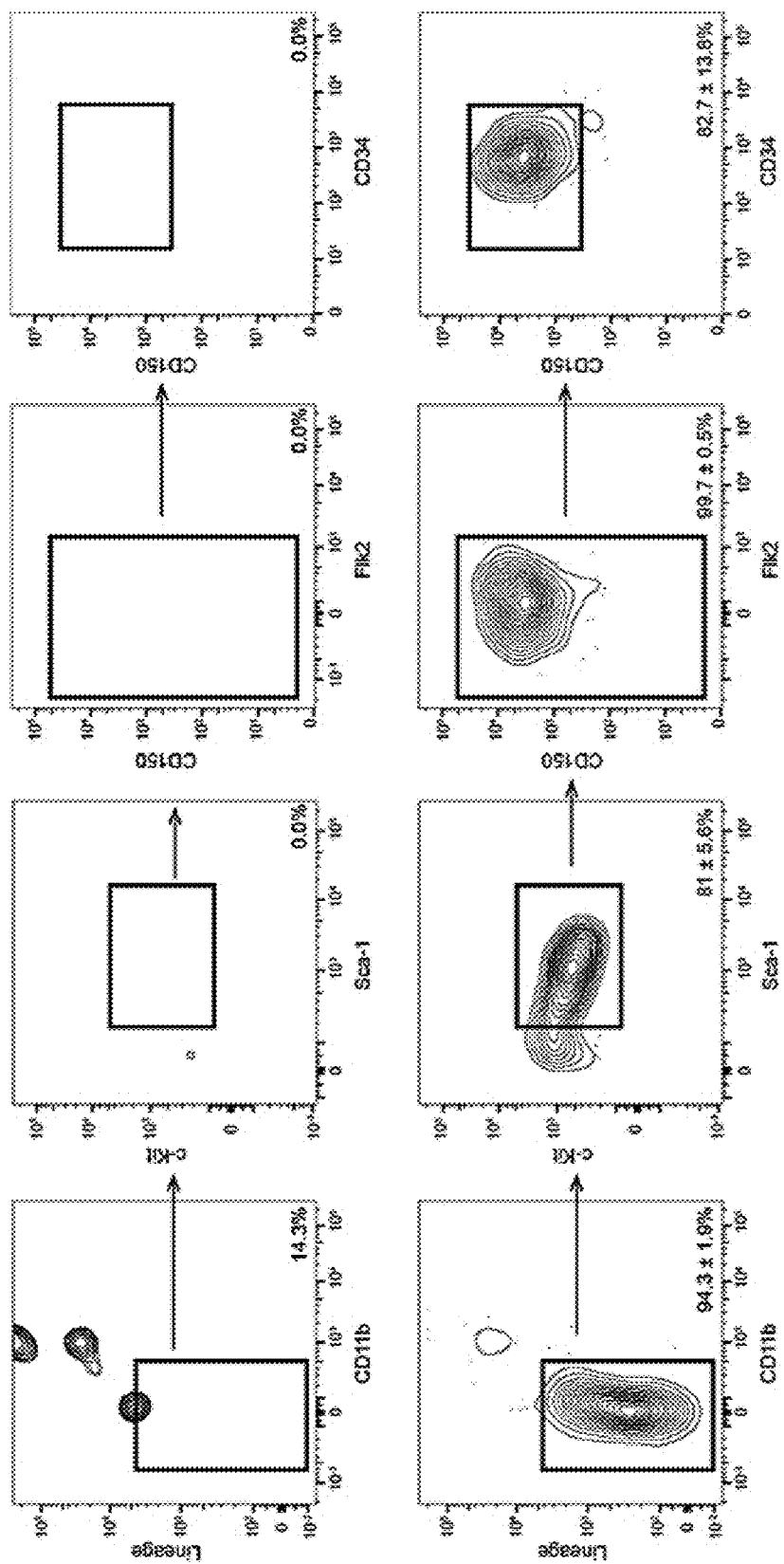
FIG. 12: Specificity of Hoxb5 as a single marker for LT-HSCs. a, Flow cytometry plots of wild type (top row) and Hoxb5-tri-mCherry (bottom row) after excluding doublets, dead cells, autofluorescence, and gating on Hoxb5+ events. Frequencies shown are percentage in gate±s.d. in each fraction (n=3 mice).

To evaluate these two possibilities, we carried out a secondary transplantation of whole bone marrow from primary $Hoxb5^{hi}$, $Hoxb5^{neg}$, or $Hoxb5^{neg}$ pHSC recipients into lethally irradiated secondary recipients (FIG. 2a). Sixteen weeks after secondary transplantation, peripheral blood analyses revealed robust multilineage chimaerism from all $Hoxb5^{hi}$ and $Hoxb5^{lo}$ transplant recipients, with minimal chimaerism from the $Hoxb5^{neg}$ fraction (FIG. 2c, e and FIG. 9b). Furthermore, bone marrow analysis of primary recipients for donor pHSCs revealed that the $Hoxb5^{hi}$ pHSC recipients contained $Hoxb5^{hi}$, $Hoxb5^{lo}$, and $Hoxb5^{neg}$ cells (100%, n=10 mice), whereas the recipients of $Hoxb5^{neg}$ cells were only $Hoxb5^{neg}$ (36%, n=4 mice) or devoid of donor cells (64%, n=7 mice). These results further suggested that the $Hoxb5^{neg}$ pHSCs were in fact transiently self-renewing ST-HSCs/MPPs. To determine if Hoxb5 expression could also distinguish LT-HSCs in a primary transplant, we normalized the number of donor cells used for secondary transplant by sorting 100 Lin-c-Kit+Sca-1+ (LSK) donor cells from the primary Hoxb5hi recipients and transplanted them into irradiated secondary recipients (n=24 mice) (FIG. 2a). As with the primary bone marrow transplantations, the chimaerism was minimal in Hoxb5-compared to Hoxb5+ recipients (FIG. 10d). Limiting dilution analysis revealed that the frequency of long-term plus short-term HSCs in primary hosts at 16 weeks was 1 in 2.1 for $Hoxb5^{hi}$, 1 in 2.4 for $Hoxb5^{lo}$, and 1 in 16.1 for $Hoxb5^{neg}$ recipients (FIG. 10). Taken together, these results demonstrate that Hoxb5 labels functional LT-HSCs.

Given that Hoxb5- cells are non-LT-HSCs, we re-examined the specificity of past definitions (FIG. 3a, f), including previously reported refinements to the LT-HSC immunophenotype and the most widely used in situ definition over the past decade. We found that 78.5%±2.6% of CD11a-HSCs, 63.9%±3% of the HSC-1 (Lin-c-Kit+Sca-1+CD48-CD150+CD229-CD244-), and 82.5%±0.4% of fraction I HSCs (Lin-c-Kit+Sca-1+CD34-/loCD150+CD41-) were Hoxb5-(FIGS. 3b, c, and d, respectively). Surprisingly, 91.3%±0.4% of Lin-CD48-CD41-CD150+ cells were Hoxb5- (FIG. 3e). As this subset was initially used for localization of HSCs in situ, we re-examined the in situ location of HSCs using Hoxb5 expression.

Visualizing LT-HSCs in bone marrow and identifying the cellular constituents and structures of the HSC niche remains challenging. Despite this, multiple constituent cell types have been proposed, including mesenchymal stromata, endosteal osteoblasts, glia, endothelia, and pericytes. In situ studies are made difficult by several technical limitations, including the number of fluorescent colours, difficulty in identifying HSCs surrounded by non-HSCs, and difficulty in translating the same fluorescently defined positive and negative thresholds from flow cytometry to tissue sections.

To address these issues, we used the Hoxb5-tri-mCherry reporter. Using flow cytometry, we determined the utility of Hoxb5 alone in identifying LT-HSCs. After logical exclusion of autofluorescence by comparison to wild-type control mice, we found that all Hoxb5+ events are within the c-Kit+ fraction and 62.0±12.8% of all Hoxb5+ events are located in the pHSC gate (12), representing an eight- to nine-fold enrichment compared to previous in situ labelling of HSCs (Lin-CD48-CD41-CD150+)(FIG. 3e).

Figure 13A:
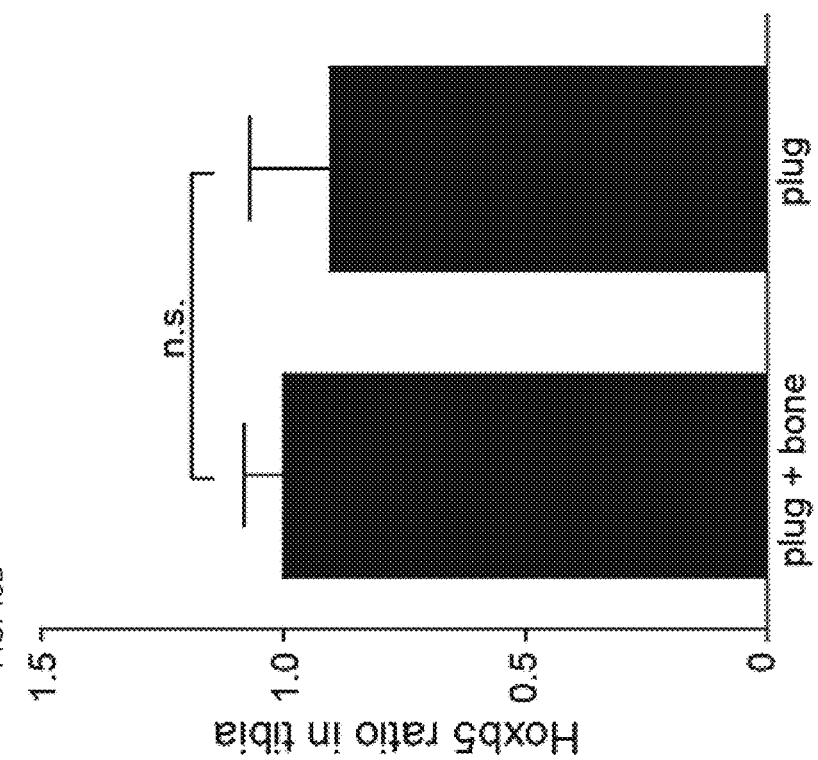
FIG. 13A-13B: Comparison of processing methods on pHSC and Hoxb5+ LT-HSC yield.
Figure 13B:
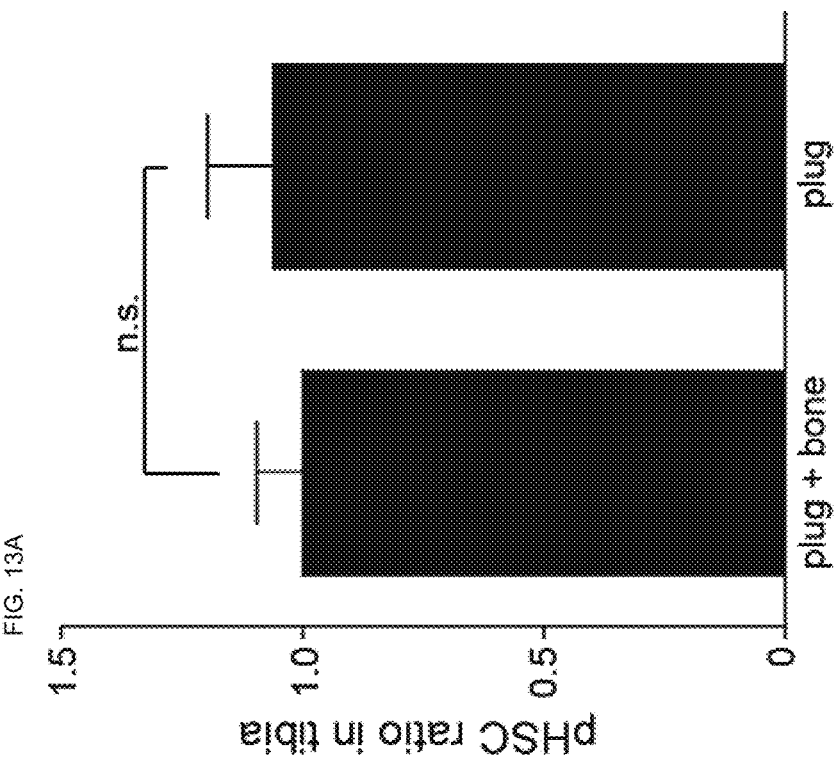

To reveal the three-dimensional (3D) HSC niche architecture, we applied the CUBIC technique (clear, unobstructed brain imaging cocktails and computational analysis) to tibial bone marrow, facilitating depletion of autofluorescent cellular components (FIG. 4a). Given that fluorescence intensity is preserved by CUBIC, the specificity of LT-HSCs in situ correlates with Hoxb5 intensity determined by flow cytometry. Therefore, on the basis of the number of Hoxb5+ LT-HSCs detected in one tibia (FIG. 13a, b), we objectively gated the same number of Hoxb5+ cells by intensity as in situ Hoxb5+ cells. We observed a uniform distribution of in situ Hoxb5+ cells along the longitudinal axis of the tibia (FIG. 4e and FIG. 14a-c). The average percentage of in situ Hoxb5+ cells was 30.8±5.9 in the proximal epiphysis, 39.0±2.4 in the diaphysis, and 30.1±5.4 in the distal epiphysis per field ($1.25\times1.25\times0.4$ mm$^3$) (FIG. 4e).

To investigate the association of LT-HSCs with vasculature, we injected anti-mouse VE-cadherin antibody into reporter mice and analysed the bone marrow with CUBIC. We found that 94.1±1.9% of in situ Hoxb5+ cells were directly attached to the abluminal surface of VE-cadherin+ endothelial cells. In contrast, only 52.8±2.3% of the random (Hoxb5-) spots were directly associated with VE-cadherin+ cells. This implied a near-homogenous perivascular location for the LT-HSC niche (FIG. 4b-d).

Following the first successful enrichment of HSCs in 1988, many groups have attempted to identify surface markers to isolate LT-HSCs. Identification of CD150, CD34, and CD48 enabled isolation of LT/ST-HSCs from MPPs. However, complete separation of LT-HSCs from ST-HSCs has never been fully accomplished. Our study demonstrates that Hoxb5 expression is specifically limited to LT-HSCs in adult mouse bone marrow. Limiting dilution assay shows that at least 1 in 2.1 of $Hoxb5^{hi}$ cells are LT-HSCs. However, this assay underestimates the functional potential of candidate HSCs. Transplantation, although the gold standard for prospective isolation of HSCs, may not take into account differences between sessile and mobile HSCs, cell cycle status, expression of CD47 (an anti-phagocytic molecule expressed highly on mobilized HSCs but at low levels on sessile bone marrow HSCs), irradiation, and their influence on engraftment efficiency.

Our results demonstrate that the LT-HSCs compartment is near-homogenously perivascular. Although other compartments have been implicated, including less homogenous association of candidate HSCs with the vasculature, it is likely that our results differ owing to the fraction of assayed populations that are LT-HSCs (FIG. 5b). These results demonstrate that the model of Hoxb5-tri-mCherry is the most specific available for identification of LT-HSCs, and can facilitate in situ lineage tracing to define their role in hematopoiesis in the absence of transplantation into irradiated hosts.

Methods

Data Reporting. No statistical methods were used to predetermine sample size. The experiments were not randomized and the investigators were not blinded to outcome assessment.

Mice. Eight-to-twelve-week-old C57BL/6J male mice (Jackson Laboratory) were used as wild-type controls.

Eight-to-twelve-week-old male B6.SJL-Ptprc$^a$ Pepc$^b$/BoyJ mice (Jackson Laboratory) were used as recipients for transplantation assay. Supporting cells for competitive reconstitution assays were collected from B6.SJL-Ptprc$^a$-Pepc$^b$/BoyJ×C57BL/6J (F$_1$ mice CD45.1$^+$/CD45.2$^+$). Mice were bred at our animal facility according to NIH guidelines. All animal protocols were approved by the Stanford University Administrative Panel on Laboratory Animal Care. Hoxb5-tri-mCherry (C57BL/6J background) mice were used as donor cells for transplantation as well as for analysis. Please see Gene targeting for mouse derivation.

Microarray data. All microarray data employed in this study are available at Gene Expression Commons and GEO. Two to four microarray replicates were assessed for each distinct cell population. The immunophenotype definition of each fraction is included in Table 1.

RNA sequencing. RNA sequencing was performed as previously describe$^-$. In brief, total RNA was isolated with trizol, treated with RQ1 RNase free DNase (Promega) to remove minute quantities of genomic DNA if present, and cleaned up using RNeasy minelute columns (QIAGEN). cDNA libraries were prepared for pHSC, MPPa, and MPPb populations using Ovation RNA-Seq System V2 (NuGen) and sequenced separately using HiSeq 2500 (Illumina) to obtain 2×150 base pair (bp) paired-end reads. Raw transcriptome sequence data were mapped to Mus musculus reference mRNAs using OLego to produce a reference-guided transcript assembly. Four replicates were sequenced for each population. Data are accessible at NCBI SRP068593.

Single-cell qPCR. Single cells for qPCR were processed using the Single Cell-to-CT qRT-PCR Kit (Life Technologies) as per the manufacturer's instructions. Cells were sorted directly into lysis solution in a 96-well plate, subjected to a reverse transcription reaction for cDNA synthesis, amplified for 14 cycles with pooled TaqMan Gene Expression Assays, and diluted with 1×TE buffer (pH 8.0). For real-time PCR, samples were amplified for 50 cycles of 3 s at 95° C. followed by 30 s at 60° C. using the following TaqMan probes: Mm00657672_m1 for Hoxb5; Mm03039759_s1 for Rnf208; Mm00470338_m1 for Smtnl1; and Mm99999915_g1 for Gapdh. All thermocycling was performed on a 7900HT Fast Real-Time PCR System (Applied Biosystems). Presence of a single cell was validated by a C$_t$ value of 30 or less for Gapdh.

Gene targeting. The targeting construct was cloned into pJYC (derived from pUC19, golden gate insert of TALE backbone vector, and removal of LacZ sequence). Right and left homology arms of ~700 bp were cloned by PCR from C57BL/6J genomic DNA, and the entire construct was sequence validated. BRUCE-4 embryonic stem (ES) cells (Millipore) derived from C57BL/6J mice were transfected with the targeting construct as well as bicistronic CRISPR vector PX330 expressing Cas9 and a Hoxb5-specific single guide RNA (5'-GGCUCCUCCGGAUGGGCUCA-3'). Following homologous recombination, recombinant clones were positively selected for one week with neomycin (100 µg ml$^{-1}$), transfected with an EF1α-Cre-puromycin vector, and selected for a second week with puromycin (1 µg ml$^{-1}$). Serially diluted ES colonies were then individually picked, expanded, and screened by PCR and qPCR for site-specific integration, exclusion of off-target effects, and correct copy number. After sequence validation of the targeted site, successfully targeted ES clones were used to establish chimaeras. Chimaeric mice were crossed with C57BL/6-Tyr$^{c-2j}$/J female mice to establish germline transmission.

Flow cytometry and cell sorting. Flow cytometry and cell sorting were performed on a FACS Aria II cell sorter (BD Biosciences) and analysed using FlowJo software (Tree Star). Bone marrow cells were collected from bilateral tibias, femurs, humeri, and pelvises by crushing (unless otherwise specified) using a mortar and pestle in Ca$^{2+}$- and Mg$^{2+}$-free PBS supplemented with 2% heat-inactivated bovine serum (Gibco) and 2 mM EDTA. Cells were passed through 100 µm, 70 µm, and 40 µm strainers before analysis and sorting. To enrich HSCs and progenitor populations, cells were stained with APC-conjugated anti-c-Kit (2B8) and fractionated using anti-APC magnetic beads and LS columns (both Miltenyi Biotec). c-Kit$^+$ cells were then stained with combinations of antibodies against the following surface markers: Sca-1, Flk2, CD150, CD34, IL-7R, CD16/32, and the lineage markers Ter-119, B220, CD2, CD3, CD4, CD5, CD8a, Gr-1, CD11a, CD11b, CD41, CD48, CD229, and CD244. For lymphoid populations, bone marrow cells were stained with antibodies against CD3, CD4, CD8a, CD11b, CD11c, Gr-1, NK-1.1, Ter-119, B220, c-Kit, and F4/80. For myeloid populations, cells were stained with antibodies against CD3, CD3–, CD11b, CD11c, CD19, Gr-1, NK-1.1, Ter-119, and F4/80. Antibody staining was performed at 4° C. and cells were incubated for 30 min. Cells stained with CD34 were incubated for 90 min. Before sorting or analysis, cells were stained with SYTOX Red Dead Cell Stain (Life Technologies) to assess viability as per the manufacturer's recommendations. Transplanted cells were double-sorted for purity.

Transplantations and peripheral blood analyses. B6.SJL-Ptprc$^a$ Pepc$^b$/BoyJ (Jackson Laboratory) recipient mice were lethally irradiated at a single dose of 9.1 Gy. For reconstitution assays, donor cells were first combined with 2×10$^5$ whole bone marrow supporting cells (B6.SJL-Ptprc$^a$Pepc$^b$/BoyJ×C57BL/6J F$_1$ mice CD45.1$^+$/CD45.2$^+$) in 200 µl of PBS with 2% FBS, then injected into the retro-orbital venous plexus. Peripheral blood analyses were performed at 4, 8, 12, and 16 weeks after primary and secondary transplantations. At each time point, 50 µl of blood was collected from the tail vein and added to 100 µl of PBS with 2 mM EDTA. Red blood cells were subsequently lysed using BD Pharm Lyse Buffer (BD Pharmingen), as per the manufacturer's protocol, for 3 min on ice, followed by blocking with 5 µg ml$^{-1}$ rat IgG. Leukocytes were stained with antibodies: CD45.1 (FITC), CD45.2 (PE), CD11b (BUV395), Gr-1 (Alexa-Flour700), B220 (BV786), CD3 (BV421), TCRβ (BV421), and NK-1.1 (PerCP-cy5.5).

For each mouse, the percentage of donor chimaerism in the peripheral blood was defined as the percentage of CD45.1$^-$CD45.2$^+$ cells among total CD45.1$^-$CD45.2$^+$ and CD45.1$^+$CD45.2$^+$ cells. To control for variability in host response to lethal irradiation, mice with host chimaerism of 50% or higher 16 weeks after transplantation were excluded from our analyses. The frequency of chimaerism in peripheral blood was analysed as follows. For evaluation of donor (CD45.1$^-$CD45.2$^+$) chimaerism kinetics, after exclusion of recipient (CD45.1$^+$CD45.2$^-$) fraction, the frequency of the donor fraction was calculated. Within the whole donor fraction, the frequency of each lineage (NK cell, B cell, T cell, granulocyte, and monocyte) was determined. For evaluation of lineage contribution kinetics, after gating each lineage, the frequency of the donor fraction (CD45.1$^-$CD45.2$^+$) was calculated. Any recipients that exhibited lower than 1% of chimaerism were treated as negative to exclude ambiguous cases.

Limiting dilution analysis The frequency of long-term and short-term HSCs was calculated using the transplantation data of ten- and three-cell Hoxb5$^{hi}$, Hoxb5$^{lo}$, or Hoxb5$^{neg}$ pHSC transplants. Any mice showing long-term (>16 week) multilineage reconstitution (>1% in each lineage) were counted as positive recipients. A nonlinear regression semi-log best fit line was used to calculate the frequency of LT/ST-HSCs at $F_0$=0.368 (GraphPad Prism 6).

CUBIC bone marrow imaging. Bone clearing protocol was modified from the original CUBIC protocol. Specifically, tibias were collected and fixed in 4% PFA solution for two days, after which bone marrow plugs were extracted from the distal end by flushing method with a 25-gauge syringe. For nuclear staining, bone marrow plugs were immersed in DAPI/PBS solution at 37° C. for three days with gentle shaking. For clearing, marrow plugs were immersed in Sca/eCUBIC-1 (Reagent-1) at 37° C. for two weeks with gentle shaking. The solution was changed every 48 h. To visualize vasculature, 20 μg of Alexa488-conjugated anti-mouse VE-cadherin antibody (BV13) was administrated intravenously (retro-orbital) with tibias collected 30 min later. Processed plugs were embedded in 4-mm-diameter glass capillaries with 2% agarose for imaging. Images were acquired using a Zeiss Z1 Lightsheet microscope (Zeiss) and reconstituted into 3D images using Zen software (Zeiss). Acquired 3D images were analysed with Imaris software (Bitplane). After exclusion of outliers including events of extraordinary size (>30 μm) or intensity, all other mCherry$^+$ (Hoxb5$^+$) cells were analysed in the tibia (n=287 cells in total from n=3 mice). The mCherry-negative threshold was determined on the basis of the intensity level of the wild-type control tibial plugs. These mCherry$^-$ events with intensities ranging from 0.002-75.998 (75.998 representing the upper bound of mCherry intensity) were transformed into an integer list of 75,000 values (75,000 representing the length of the list), and 600 spots were then randomly selected from this integer list using the 'randbetween' (1,75,000) function in Excel 2015 (Microsoft). Using the list of random spots identified by intensity, the location and distance to VE-cadherin$^+$ cells was measured using the Imaris software. All CUBIC imaging experiments were performed in biological triplicates from three mice.

Genotyping. Genomic DNA from Hoxb5-tri-mCherry mice was isolated from tail biopsies using QuickExtract solution (EpiCentre). PCR amplification was performed using the same forward primer (5'-GACGTATCGA-GATCGCCCAC-3') with two reverse primers to distinguish between the Hoxb5-tri-mCherry (5'-CCTTGGTCACCT-TCAGCTTGG-3') and wild-type (5'-AGATTG-GAAGGGTCGAGCTG-3') alleles.

Statistics. All comparative analyses were performed using unpaired Student's t tests. Pearson's chi-square test was performed using online software.

Morrison, S. J. & Scadden, D. T. The bone marrow niche for hematopoietic stem cells. *Nature* 505, 327-334 (2014)

Dykstra, B. et al. Long-term propagation of distinct hematopoietic differentiation programs in vivo. *Cell Stem Cell* 1, 218-229 (2007)

Beerman, I. et al. Functionally distinct hematopoietic stem cells modulate hematopoietic lineage potential during aging by a mechanism of clonal expansion. *Proc. Natl Acad. Sci. USA* 107, 5465-5470 (2010)

Lu, R., Neff, N. F., Quake, S. R. & Weissman, I. L. Tracking single hematopoietic stem cells in vivo using high-throughput sequencing in conjunction with viral genetic barcoding. *Nature Biotechnol.* 29, 928-933 (2011)

Uchida, N. & Weissman, I. L. Searching for hematopoietic stem cells: evidence that Thy-1.1$^{lo}$Lin$^-$Sca-1$^+$ cells are the only stem cells in C57BL/Ka-Thy-1.1 bone marrow. *J. Exp. Med.* 175, 175-184 (1992)

Acar, M. et al. Deep imaging of bone marrow shows non-dividing stem cells are mainly perisinusoidal. *Nature* 526, 126-130 (2015)

Gazit, R. et al. hoxb5 identifies hematopoietic stem cells in the murine bone marrow. *J. Exp. Med.* 211, 1315-1331 (2014)

Hills, D. et al. Hoxb4-YFP reporter mouse model: a novel tool for tracking HSC development and studying the role of Hoxb4 in hematopoiesis. *Blood* 117, 3521-3528 (2011)

Yamamoto, R. et al. Clonal analysis unveils self-renewing lineage-restricted progenitors generated directly from hematopoietic stem cells. *Cell* 154, 1112-1126 (2013)

Fathman, J. W. et al. Upregulation of CD11A on hematopoietic stem cells denotes the loss of long-term reconstitution potential. *Stem Cell Reports* 3, 707-715 (2014)

Oguro, H., Ding, L. & Morrison, S. J. SLAM family markers resolve functionally distinct subpopulations of hematopoietic stem cells and multipotent progenitors. *Cell Stem Cell* 13, 102-116 (2013)

Forsberg, E. C. et al. Molecular signatures of quiescent, mobilized and leukemia-initiating hematopoietic stem cells. *PLoS ONE* 5, e8785 (2010)

Fleming, W. H. et al. Functional heterogeneity is associated with the cell cycle status of murine hematopoietic stem cells. *J. Cell Biol.* 122, 897-902 (1993)

Passegué, E., Wagers, A. J., Giuriato, S., Anderson, W. C. & Weissman, I. L. Global analysis of proliferation and cell cycle gene expression in the regulation of hematopoietic stem and progenitor cell fates. *J. Exp. Med.* 202, 1599-1611 (2005)

What is claimed is:

1. A transgenic mouse for analysis of long term hematopoietic stem cells (LT-HSC), comprising: a transgenic mouse whose genome comprises a transgene comprising a DNA sequence encoding a fluorescent single-color tri-mCherry protein comprising a membrane localization sequence operably linked to an endogenous Hoxb5 promoter, wherein the transgene is integrated at the endogenous Hoxb5 gene locus, wherein the sequence encoding the tri-mCherry fluorescent protein is joined to Hoxb5 coding sequence and separated by an internal ribosome entry site or self-cleaving peptide; wherein expression of the tri-mCherry fluorescent protein distinguishes between LT-HSC and non-LT-HSC and identifies substantially all LT-HSC in the bone marrow of the transgenic mouse.

2. The transgenic mouse of claim 1, wherein the mouse is heterozygous for the transgene.

3. The transgenic mouse of claim 1, wherein the mouse is homozygous for the transgene.

4. The transgenic mouse of claim 1, wherein the self-cleaving peptide sequence is a P2A self-cleaving peptide sequence.

5. A population of LT-HSC isolated from the bone marrow of the transgenic mouse of claim 1, wherein the LT-HSC are Hoxb5 positive and express the tri-mCherry fluorescent protein.

6. A method of screening a candidate agent or regimen for an effect on growth or differentiation of LT-HSC, the method comprising: contacting the transgenic mouse of claim 1, or a population of LT-HSC cells expressing the tri-mCherry fluorescent protein transgene isolated or derived from the transgenic mouse of claim 1 with the candidate agent or regimen, and determining the effect of the candidate agent or regimen on a parameter of growth or differentiation of LT-HSC which express the tri-mCherry fluorescent protein transgene.

7. The method of claim 6, wherein the effect on growth or differentiation is determined by measuring one or more of proliferation, multipotency, differentiation, self-renewal and quiescence.

* * * * *

SEQUENCE LISTING

<160> NUMBER OF SEQ ID NOS: 4

<210> SEQ ID NO 1
<211> LENGTH: 20
<212> TYPE: RNA
<213> ORGANISM: Artificial Sequence
<220> FEATURE:
<223> OTHER INFORMATION: Synthetic nucleotide

<400> SEQUENCE: 1
ggcuccuccg gaugggcuca                                            20

<210> SEQ ID NO 2

```
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 2
gacgtatcga gatcgcccac                                               20

<210> SEQ ID NO 3
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 3
ccttggtcac cttcagcttg g                                             21

<210> SEQ ID NO 4
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 4
agattggaag ggtcgagctg                                               20
```